US008741609B2

(12) United States Patent
Adams et al.

(10) Patent No.: US 8,741,609 B2
(45) Date of Patent: Jun. 3, 2014

(54) **DETERGENT COMPOSITIONS CONTAINING *GEOBACILLUS STEAROTHERMOPHILUS* LIPASE AND METHODS OF USE THEREOF**

(75) Inventors: Christian Adams, Palo Alto, CA (US); Brian Schmidt, Half Moon Bay, CA (US)

(73) Assignee: Danisco US Inc., Palo Alto, CA (US)

( * ) Notice: Subject to any disclaimer, the term of this patent is extended or adjusted under 35 U.S.C. 154(b) by 0 days.

(21) Appl. No.: 13/518,354

(22) PCT Filed: Dec. 14, 2010

(86) PCT No.: PCT/US2010/060268
§ 371 (c)(1),
(2), (4) Date: Jun. 21, 2012

(87) PCT Pub. No.: WO2011/084417
PCT Pub. Date: Jul. 14, 2011

(65) Prior Publication Data
US 2012/0309063 A1   Dec. 6, 2012

Related U.S. Application Data

(60) Provisional application No. 61/288,682, filed on Dec. 21, 2009.

(51) Int. Cl.
*C12P 21/06* (2006.01)

(52) U.S. Cl.
USPC ............................ 435/134; 435/69.1

(58) Field of Classification Search
USPC ...................................... 435/134
See application file for complete search history.

(56) References Cited

U.S. PATENT DOCUMENTS

| 4,246,612 A | 1/1981 | Berry et al. |
|---|---|---|
| 4,430,243 A | 2/1984 | Bragg |
| 4,435,307 A | 3/1984 | Barbesgaard et al. |
| 4,810,410 A | 3/1989 | Diakun et al. |
| 4,810,414 A | 3/1989 | Huge-Jensen et al. |
| 4,876,024 A | 10/1989 | Enomoto et al. |
| 4,977,252 A | 12/1990 | Chiu |
| 5,153,135 A | 10/1992 | Farin et al. |
| 5,227,084 A | 7/1993 | Martens et al. |
| 5,290,694 A | 3/1994 | Nakanishi et al. |
| RE34,606 E | 5/1994 | Estell et al. |
| 5,340,735 A | 8/1994 | Christianson et al. |
| 5,354,559 A | 10/1994 | Morehouse |
| 5,427,936 A | 6/1995 | Moeller et al. |
| 5,486,303 A | 1/1996 | Capeci et al. |
| 5,489,392 A | 2/1996 | Capeci et al. |
| 5,500,364 A | 3/1996 | Christianson et al. |
| 5,512,203 A | 4/1996 | Kolattukudy et al. |
| 5,516,448 A | 5/1996 | Capeci et al. |
| 5,565,422 A | 10/1996 | Del Greco et al. |
| 5,569,645 A | 10/1996 | Dinniwell et al. |
| 5,574,005 A | 11/1996 | Welch et al. |
| 5,576,282 A | 11/1996 | Miracle et al. |
| 5,595,967 A | 1/1997 | Miracle et al. |
| 5,597,936 A | 1/1997 | Perkins et al. |
| 5,646,101 A | 7/1997 | MacBeath |
| 5,686,014 A | 11/1997 | Baillely et al. |
| 5,691,297 A | 11/1997 | Nassano et al. |
| 5,692,650 A | 12/1997 | Wolter et al. |
| 5,695,679 A | 12/1997 | Christie et al. |
| 5,698,504 A | 12/1997 | Christie et al. |
| 5,700,676 A | 12/1997 | Bott et al. |
| 5,705,464 A | 1/1998 | Scheper et al. |
| 5,710,115 A | 1/1998 | Patel et al. |
| 5,772,786 A * | 6/1998 | De Smet et al. ............. 134/25.2 |
| 5,795,855 A | 8/1998 | Schneider et al. |
| 5,801,039 A | 9/1998 | Maurer et al. |
| 5,855,625 A | 1/1999 | Maurer et al. |
| 5,858,959 A | 1/1999 | Surutzidis et al. |
| 5,874,276 A | 2/1999 | Fowler et al. |
| 5,879,584 A | 3/1999 | Bianchetti et al. |
| 5,888,954 A | 3/1999 | Haerer et al. |
| 5,935,826 A | 8/1999 | Blue et al. |
| 5,955,340 A | 9/1999 | Bott et al. |
| 5,965,510 A | 10/1999 | Schneider et al. |
| 5,990,069 A | 11/1999 | Andre et al. |
| 6,197,589 B1 | 3/2001 | Maurer et al. |
| 6,225,464 B1 | 5/2001 | Hiler et al. |
| 6,306,812 B1 | 10/2001 | Perkins et al. |
| 6,312,936 B1 | 11/2001 | Poulose et al. |
| 6,326,348 B1 | 12/2001 | Vinson et al. |
| 6,376,450 B1 | 4/2002 | Ghosh et al. |

(Continued)

FOREIGN PATENT DOCUMENTS

| EP | 238023 | 9/1987 |
|---|---|---|
| EP | 305216 | 3/1989 |

(Continued)

OTHER PUBLICATIONS

Jaeger, K and Thorsten, E. Lipases for biotechnology, Current opinion in Biotechnology, 13: 390-397, 2002.*
Leow et al., High level expression of thermostable lipase from *Geobacillus* sp. strain T1. Biosci. Biotechnol. Biochem. 68, 96-103, 2004.*
Altschul, et al., "Basic local alignment search tool", J Mol Biol, (1990) 215:403-410.
Chang, et al., "High frequency transformation of *Bacillus subtilis* protoplasts by plasmid DNA", Mol Gen Genet, (1979), 168:111-5.
Collier, et al., "Generation and identification of variants with improved purification yield of Bowman-Birk protease inhibitors carrying protein binding loops", Protein Expr Purif, (2009), 68:146-60.

(Continued)

*Primary Examiner* — Tekchand Saidha
*Assistant Examiner* — Rama P Ramanujam
(74) *Attorney, Agent, or Firm* — Danisco US Inc.

(57) ABSTRACT

The present compositions and methods relate to a lipase cloned from *Geobacillus stearothermophilus*, polynucleotides encoding the lipase, and methods of use thereof. The compositions and methods have particular application in detergent cleaning compositions and methods.

17 Claims, No Drawings

(56) References Cited

U.S. PATENT DOCUMENTS

| | | | |
|---|---|---|---|
| 6,440,991 | B1 | 8/2002 | Zhu et al. |
| 6,482,628 | B1 | 11/2002 | Poulose et al. |
| 6,566,114 | B1 | 5/2003 | Kauppinen et al. |
| 6,599,871 | B2 | 7/2003 | Smith |
| 6,602,842 | B2 | 8/2003 | Cuperus et al. |
| 6,605,458 | B1 | 8/2003 | Hansen et al. |
| 6,610,642 | B2 | 8/2003 | Ghosh et al. |
| 7,122,334 | B2 | 10/2006 | Schellenberger et al. |
| 7,319,029 | B2 * | 1/2008 | Rahman et al. ............ 435/252.3 |
| 8,008,241 | B2 | 8/2011 | Souter |
| 8,080,044 | B2 | 12/2011 | Biedermann et al. |
| 8,114,656 | B2 | 2/2012 | Shaw et al. |
| 8,298,799 | B2 | 10/2012 | Bornscheuer et al. |
| 2005/0196766 | A1 | 9/2005 | Soe et al. |
| 2006/0078648 | A1 | 4/2006 | De Kreij et al. |
| 2006/0154843 | A1 | 7/2006 | Wang et al. |
| 2007/0026106 | A1 | 2/2007 | Kreij et al. |
| 2008/0004201 | A1 | 1/2008 | Boutique et al. |
| 2008/0090747 | A1 | 4/2008 | Augustinus et al. |
| 2008/0145353 | A1 | 6/2008 | Amin et al. |
| 2009/0325240 | A1 * | 12/2009 | Daniell ........................ 435/101 |

FOREIGN PATENT DOCUMENTS

| | | |
|---|---|---|
| EP | 0495257 | 7/1992 |
| GB | 1296839 | 11/1972 |
| GB | 1372034 | 10/1974 |
| JP | 64-074992 | 3/1989 |
| WO | WO90/09446 | 8/1990 |
| WO | WO92/06154 | 4/1992 |
| WO | WO00/32601 | 6/2000 |
| WO | WO00/37602 | 6/2000 |
| WO | WO2008/032007 | 3/2008 |

OTHER PUBLICATIONS

Dartois, et al., "Cloning, nucleotide sequence and expression in *Escherichia coli* of a lipase gene from *Bacillus subtilis* 168", Biochim Biophys Acta, (1992), 1131:253-60.

Ferrari, et al., "Genetics", *Bacillus*, (1989), pp. 57-72.

Gupta, et al., "Lipase assays for conventional and molecular screening: an overview", Biotechnol Appl Biochem, (2003), 37:63-71.

Haas, et al., "Cloning, expression and characterization of a cDNA encoding a lipase from *Rhizopus delemar*", Gene, (1991), 109:107-13.

Henikoff, et al., "Amino acid substitution matrices from protein blocks", Proc Natl Acad Sci, (1992), 89:10915-9.

Iiiggins, et al., "Clustal: a package for performing multiple sequence alignment on a microcomputer", Gene, (1988), 73:237-44.

Karlin, et al., "Applications and statistics for multiple high-scoring segments in molecular sequences", Proc Natl Acad Sci, (1993), 90:5873-7.

Kugimiya, et al., "Cloning and sequence analysis of cDNA encoding *Rhizopus niveus* lipase", Biosci Biotechnol Biochem, (1992), 56:716-9.

Leow, et al., "A thermoalkaliphilic lipase of *Geobacillus* sp. T1", Extremophiles, (2007), 11:527-35.

Leow, et al., "High level expression of thermostable lipase from *Geobacillus* sp. strain T1", Biosci Biotechnol Biochem, (2004), 68:96-103.

Minolta (Firma Comercial), "Precise Color Communication: Color Control From Perception to Instrumentation", Konica Minolta Sensing, Inc., (1998), pp. 32-50.

Pearson, et al., "Improved tools for biological sequence comparison", Prov Natl Acad Sci, (1988), 85:2444-8.

Shimada, et al., "cDNA molecular cloning of *Geotrichum candidum* lipase", J Biochem., (1989), 106:383-8.

Smith, et al., "Protoplast transformation in coryneform bacteria and introduction of an alpha-amylase gene from *Bacillus amyloliquefaciens* into *Brevibacterium lactofermentum*", Appl Environ Microbiol, (1986), 51:634-9.

Vogtentanz, et al., "A *Bacillus subtilis* fusion protein system to produce soybean Bowman-Birk protease inhibitor", Protein Expr Purif, (2007), 55:40-52.

Yamaguciii, et al., "Cloning and structure of the mono- and diacylglycerol lipase-encoding gene from *Penicillium camembertii* U-150", Gene, (1991), 103:61-7.

Database Geneseq, GSP: AEH47562, "Environmental isolate hydrolase, Seq ID No. 622", (2006) http://www.ebi.ac.uk/ena/data/view/AEH47562&display=text.

Rahman, et al., "Geobacillus zalihae sp. nov., a thermophilic lipolytic bacterium isolated from palm oil mill effluent in Malaysia", BMC Microbiol, (2007), 7:77.

\* cited by examiner

**DETERGENT COMPOSITIONS CONTAINING *GEOBACILLUS STEAROTHERMOPHILUS* LIPASE AND METHODS OF USE THEREOF**

PRIORITY

The present application claims priority to U.S. Provisional Application Ser. No. 61/288,682, filed on Dec. 21, 2009, which is hereby incorporated by reference in its entirety

TECHNICAL FIELD

The present compositions and methods relate to a lipase cloned from *Geobacillus stearothermophilus*, polynucleotides encoding the lipase, and methods of use thereof.

BACKGROUND

Current laundry detergent and/or fabric care compositions include a complex combination of active ingredients such as surfactants, enzymes (protease, amylase, lipase, and/or cellulase), bleaching agents, a builder system, suds suppressors, soil-suspending agents, soil-release agents, optical brighteners, softening agents, dispersants, dye transfer inhibition compounds, abrasives, bactericides, and perfumes.

Lipolytic enzymes, including lipases and cutinases, have been employed in detergent cleaning compositions for the removal of oily stains by hydrolyzing triglycerides to generate fatty acids. However, these enzymes are often inhibited by surfactants and other components present in cleaning composition, interfering with their ability to remove oily stains. Accordingly, the need exists for lipases and cutinases that can function in the harsh environment of cleaning compositions.

There also exists a need for more robust and efficient lipases and cutinases that are effective in performing transesterification reactions for the production of biofuels, lubricants, and other synthetic and semi-synthetic hydrocarbons. Preferably, such enzymes will utilize naturally occurring or commonly available starting materials and will not require protection and deprotection steps in a synthesis reaction, which complicate the synthesis and lead to the production of toxic waste products.

SUMMARY

The present compositions and methods relate to a thermostable lipase cloned from *Geobacillus stearothermophilus* strain T1 (GeoT1). In some embodiments, GeoT1 is fused to the carboxy-terminus of the catalytic domain of a bacterial cellulase. In some embodiments, the bacterial cellulase is derived from a *Bacillus* strain deposited as CBS 670.93 (referred to as BCE103) with the Central Bureau voor Schimmelcultures, Baam, The Netherlands. In some embodiments, GeoT1 is connected to the BCE103 cellulase by a cleavable linker. Thus in some embodiments, GeoT1 is not a fusion protein.

In one aspect of the disclosure, a recombinant *G. stearothermophilus* GeoT1 polypeptide is provided. In some embodiments, the recombinant GeoT1 polypeptide is from 80% to 99% identical (e.g., 80%, 85%, 90%, 91%, 92%, 93%, 94%, 95%, 96%, 97%, 98%, or 99% identical) to the amino acid sequence of SEQ ID NO: 4. In further embodiments, the recombinant GeoT1 polypeptide is a fusion protein comprising a BCE103 cellulase amino-terminal fragment. In some embodiments, the recombinant GeoT1 fusion protein is at least 80% identical (e.g., 80%, 85%, 90%, 91%, 92%, 93%, 94%, 95%, 96%, 97%, 98%, 99% or 100% identical) to the amino acid sequence of SEQ ID NO: 5. Unless specifically indicated, as used herein the term GeoT1 polypeptide encompasses both GeoT1 fusion proteins, as well as mature GeoT1 polypeptides lacking a fusion partner. In some embodiments, the GeoT1 polypeptide is expressed in *Bacillus subtilis*. In other embodiments, the Geot1 polypeptide is expressed in *Streptomyces lividans*. The present disclosure also provides an expression vector comprising a polynucleotide encoding the GeoT1 polypeptide in operable combination with a promoter.

In a preferred aspect of the disclosure, a detergent composition comprising a recombinant *G. stearothermophilus* GeoT1 polypeptide is provided. In some embodiments, the recombinant GeoT1 polypeptide is at least 80% identical (e.g., 80%, 85%, 90%, 91%, 92%, 93%, 94%, 95%, 96%, 97%, 98%, 99% or 100% identical) to the amino acid sequence of SEQ ID NO: 4. In further embodiments, the recombinant GeoT1 polypeptide is a fusion protein comprising a BCE103 cellulase amino-terminal fragment. In some embodiments, the recombinant GeoT1 fusion protein is at least 80% identical (e.g., 80%, 85%, 90%, 91%, 92%, 93%, 94%, 95%, 96%, 97%, 98%, 99% or 100% identical) to the amino acid sequence of SEQ ID NO: 5. In some preferred embodiments, the composition comprises a surfactant (ionic or non-ionic). In some embodiments, the surfactant comprises one or more of the group consisting of sodium dodecyl benzene sulfonate, sodium hydrogenated cocoate, sodium laureth sulfate, C12-14 pareth-7, C12-15 pareth-7, sodium C12-15 pareth sulfate, C14-15 pareth-4. In some embodiments, the surfactant comprises an ionic surfactant. In some preferred embodiments, the ionic surfactant is selected from the group consisting of an anionic surfactant, a cationic surfactant, a zwitterionic surfactant, and a combination thereof. In some embodiments, the detergent is formulated at a pH of from 8.0 to 10.0. In some embodiments, the detergent is selected from the group consisting of a laundry detergent, a dishwashing detergent, and a hard-surface cleaning detergent. In some embodiments, the detergent is in a form selected from the group consisting of a liquid, a powder, a granulated solid, and a tablet. In particularly preferred embodiments, the GeoT1 polypeptide has enzymatic activity in the detergent at a temperature from 30° C. to 40° C.

In a related aspect, a detergent composition is provided, comprising: a lipase from *Geobacillus stearothermophilus*, and a surfactant, wherein the detergent composition is more effective in removing oily stains from a surface to be cleaned than the detergent composition in the absence of the lipase.

In some embodiments, the lipase is from *G. stearothermophilus* strain T1. In some embodiments, the lipase is GeoT1 lipase. In some embodiments, the GeoT1 polypeptide is a fusion protein comprising a BCE103 cellulase amino-terminal fragment. In some embodiments, the lipase comprises an amino acid sequence having at least 90% amino acid sequence identity to SEQ ID NO: 4 or SEQ ID NO: 5. In some embodiments, the lipase comprises an amino acid sequence having at least 95% amino acid sequence identity to SEQ ID NO: 4 or SEQ ID NO: 5.

In some embodiments, the lipase is a recombinant lipase. In some embodiments, the lipase is a recombinant lipase expressed in *Bacillus subtilis*. In some embodiments, the lipase is a recombinant lipase expressed in *Streptomyces lividans*.

In some embodiments, the surfactant is an ionic or a non-ionic surfactant. In some embodiments, the surfactant is one or more surfactants selected from the group consisting of an anionic surfactant, a cationic surfactant, a zwitterionic surfactant, and a combination thereof. In some embodiments, the surfactant comprises one or more surfactants selected from the group consisting of sodium dodecyl benzene sulfonate, sodium hydrogenated cocoate, sodium laureth sulfate, C12-14 pareth-7, C12-15 pareth-7, sodium C12-15 pareth sulfate, and C14-15 pareth-4.

In some embodiments, the detergent composition is formulated at a pH of from about 8.0 to about 10.0. In some embodiments, the detergent composition is formulated at a pH of from about 8.2 to about 10.0.

In some embodiments, the detergent composition is selected from the group consisting of a laundry detergent, a dishwashing detergent, and a hard-surface cleaning detergent. In some embodiments, the form of the composition is selected from the group consisting of a liquid, a powder, a granulated solid, and a tablet.

In some embodiments, the detergent composition is effective in hydrolyzing a lipid at a temperature of from about 30° C. to about 40° C.

In some embodiments, the detergent composition is more effective in hydrolyzing C4 to C16 substrates compared to an equivalent detergent composition comprising *Pseudomonas pseudoalcaligenes* lipase variant M21L (LIPOMAX™) in place of *G. stearothermophilus* lipase.

In some embodiments, the detergent composition further comprises a protease. In some embodiments, the detergent composition comprises a subtilisin protease.

In another aspect, a method for hydrolyzing a lipid present in a soil or stain on a surface is provided, comprising contacting the surface with a detergent composition comprising a recombinant GeoT1 polypeptide and a surfactant. The detergent compositions of the preceding paragraph, the description, and the examples are suitable for this purpose.

In a further aspect, a method for performing a transesterification reaction is provided, comprising contacting a donor molecule with a composition comprising a recombinant GeoT1 polypeptide. In some embodiments, the donor molecule has a C4-16 carbon chain. In a preferred embodiment, the donor molecule has a C8 carbon chain.

These and other aspects of GeoT1 compositions and methods will be apparent from the following description.

DETAILED DESCRIPTION

I. Introduction

Described are compositions and methods relating to a thermostable lipase cloned from *Geobacillus stearothermophilus* strain T1 (GeoT1). The compositions and methods are based, in part, on the observation that cloned and expressed GeoT1 has carboxylic ester hydrolase activity in the presence of a detergent compositions. This feature of GeoT1 makes it well suited for use in a variety of cleaning applications, where the enzyme can hydrolyze lipids in the presence of surfactants and other components found in detergent compositions.

While GeoT1 shows activity against a variety of natural and synthetic substrates, the enzyme has shown a preference for C4-C16 substrates, with peak activity against C8 substrates. This specificity makes GeoT1 well suited for hydrolysis of short-chain triglycerides and for performing transesterification reactions involving short-chain fatty acids.

II. Definitions

Prior to describing the present compositions and methods in detail, the following terms are defined for clarity. Terms and abbreviations not defined should be accorded their ordinary meaning as used in the art:

As used herein, a "a carboxylic ester hydrolase" (E.C. 3.1.1) refers to an enzyme that acts on carboxylic acid esters.

As used herein, a "lipase", "lipase enzyme", "lipolytic enzymes", "lipolytic polypeptides", or "lipolytic proteins" refers to an enzyme, polypeptide, or protein exhibiting a lipid degrading capability such as a capability of degrading a triglyceride or a phospholipid. The lipolytic enzyme may be, for example, a lipase, a phospholipase, an esterase or a cutinase. As used herein, lipolytic activity may be determined according to any procedure known in the art (see, e.g., Gupta et al., *Biotechnol Appl. Biochem.*, 37:63-71, 2003; U.S. Pat. No. 5,990,069; and International Publication No. WO 96/1 8729A1).

As used herein, the term "fatty acid" refers to a carboxylic acid derived from or contained in an animal or vegetable fat or oil. Fatty acids are composed of a chain of alkyl groups typically containing from 4-22 carbon atoms and characterized by a terminal carboxyl group (—COOH). Fatty acids may be saturated or unsaturated, and solid, semisolid, or liquid.

As used herein, the term "triglyceride" refers to any naturally occurring ester of a fatty acid and glycerol. Triglycerides are the chief constituents of fats and oils. The have the general formula of $CH_2(OOCR_1)CH(OOCR_2)CH_2(OOCR_3)$, where $R_1$, $R_2$, and $R_3$ may be of different chain length.

As used herein, "acyl" is the general name for an organic acid group (RCO—), generally obtained by removing the —OH group from a carboxylic acid.

As used herein, the term "acylation" refers to a chemical transformation which substitutes/adds an acyl group into a molecule, generally at the side of an —OH group.

As used herein, an "acyl chain substrate" is a donor molecule for a carboxylic ester hydrolase (e.g., cutinase, lipase, acyltransferase, transesterase, and the like). The substrate may be described in terms of its carbon-chain length. For example, a C4 substrate/donor has a chain-length of 4 carbons, a C8 substrate/donor has a chain-length of 8 carbons, and the like.

As used herein, the term "transferase" refers to an enzyme that catalyzes the transfer of a molecule or group (e.g., an acyl group) to a substrate.

As used herein, "leaving group" refers to the nucleophile which is cleaved from the acyl donor upon substitution by another nucleophile.

As used herein, the phrase "detergent stability" refers to the stability of a specified detergent composition component (such as a hydrolytic enzyme) in a detergent composition mixture.

As used herein, a "perhydrolase" is an enzyme capable of catalyzing a reaction that results in the formation of a peracid suitable for applications such as cleaning, bleaching, and disinfecting.

As used herein, the term "aqueous," as used in the phrases "aqueous composition" and "aqueous environment," refers to a composition that is made up of at least 50% water. An aqueous composition may contain at least 50% water, at least 60% water, at least 70% water, at least 80% water, at least 90% water, at least 95% water, at least 97% water, at least 99% water, or even at least 99% water.

As used herein, the term "surfactant" refers to any compound generally recognized in the art as having surface active qualities. Surfactants generally include anionic, cationic, nonionic, and zwitterionic compounds, which are further described, herein.

As used herein, "surface property" is used in reference to electrostatic charge, as well as properties such as the hydrophobicity and hydrophilicity exhibited by the surface of a protein.

The term "oxidation stability" refers to lipases of the present disclosure that retain a specified amount of enzymatic activity over a given period of time under conditions prevailing during the lipolytic, hydrolyzing, cleaning or other process disclosed herein, for example while exposed to or contacted with bleaching agents or oxidizing agents. In some embodiments, the lipases retain at least about 50%, about 60%, about 70%, about 75%, about 80%, about 85%, about 90%, about 92%, about 95%, about 96%, about 97%, about 98%, or about 99% lipolytic activity after contact with a bleaching or oxidizing agent over a given time period, for example, at least about 1 minute, about 3 minutes, about 5 minutes, about 8 minutes, about 12 minutes, about 16 minutes, about 20 minutes, etc.

The term "chelator stability" refers to lipases of the present disclosure that retain a specified amount of enzymatic activity over a given period of time under conditions prevailing during the lipolytic, hydrolyzing, cleaning or other process disclosed herein, for example while exposed to or contacted with chelating agents. In some embodiments, the lipases retain at least about 50%, about 60%, about 70%, about 75%, about 80%, about 85%, about 90%, about 92%, about 95%, about 96%, about 97%, about 98%, or about 99% lipolytic activity after contact with a chelating agent over a given time period, for example, at least about 10 minutes, about 20 minutes, about 40 minutes, about 60 minutes, about 100 minutes, etc.

The terms "thermal stability" and "thermostable" refer to lipases of the present disclosure that retain a specified amount of enzymatic activity after exposure to identified temperatures over a given period of time under conditions prevailing during the lipolytic, hydrolyzing, cleaning or other process disclosed herein, for example while exposed altered temperatures. Altered temperatures include increased or decreased temperatures. In some embodiments, the lipases retain at least about 50%, about 60%, about 70%, about 75%, about 80%, about 85%, about 90%, about 92%, about 95%, about 96%, about 97%, about 98%, or about 99% lipolytic activity after exposure to altered temperatures over a given time period, for example, at least about 60 minutes, about 120 minutes, about 180 minutes, about 240 minutes, about 300 minutes, etc.

The term "cleaning activity" refers to the cleaning performance achieved by the lipase under conditions prevailing during the lipolytic, hydrolyzing, cleaning or other process disclosed herein. In some embodiments, cleaning performance is determined by the application of various cleaning assays concerning enzyme sensitive stains, for example grass, blood, milk, or egg protein as determined by various chromatographic, spectrophotometric or other quantitative methodologies after subjection of the stains to standard wash conditions. Exemplary assays include, but are not limited to those described in WO 99/34011, and U.S. Pat. No. 6,605,458 (both of which are herein incorporated by reference), as well as those methods included in the examples.

The term "cleaning effective amount" of a lipase refers to the quantity of lipase described hereinbefore that achieves a desired level of enzymatic activity in a specific cleaning composition. Such effective amounts are readily ascertained by one of ordinary skill in the art and are based on many factors, such as the particular lipase used, the cleaning application, the specific composition of the cleaning composition, and whether a liquid or dry (e.g., granular, bar) composition is required etc.

The term "cleaning adjunct materials," as used herein, means any liquid, solid or gaseous material selected for the particular type of cleaning composition desired and the form of the product (e.g., liquid, granule, powder, bar, paste, spray, tablet, gel; or foam composition), which materials are also preferably compatible with the lipase enzyme used in the composition. In some embodiments, granular compositions are in "compact" form, while in other embodiments, the liquid compositions are in a "concentrated" form.

As used herein, "cleaning compositions" and "cleaning formulations" refer to admixtures of chemical ingredients that find use in the removal of undesired compounds (e.g., soil or stains) from items to be cleaned, such as fabric, dishes, contact lenses, other solid surfaces, hair, skin, teeth, and the like. The composition or formulations may be in the form of a liquid, gel, granule, powder, or spray, depending on the surface, item or fabric to be cleaned, and the desired form of the composition or formulation.

As used herein, the terms "detergent composition" and "detergent formulation" refer to mixtures of chemical ingredients intended for use in a wash medium for the cleaning of soiled objects. Detergent compositions/formulations generally include at least one surfactant, and may optionally include hydrolytic enzymes, oxido-reductases, builders, bleaching agents, bleach activators, bluing agents and fluorescent dyes, caking inhibitors, masking agents, enzyme activators, antioxidants, and solubilizers.

As used herein, "dishwashing composition" refers to all forms of compositions for cleaning dishware, including cutlery, including but not limited to granular and liquid forms. In some embodiments, the dishwashing composition is an "automatic dishwashing" composition that finds use in automatic dish washing machines. It is not intended that the present disclosure be limited to any particular type or dishware composition. Indeed, the present disclosure finds use in cleaning dishware (e.g., dishes, including, but not limited to plates, cups, glasses, bowls, etc.) and cutlery (e.g., utensils, including but not limited to spoons, knives, forks, serving utensils, etc.) of any material, including but not limited to ceramics, plastics, metals, china, glass, acrylics, etc. The term "dishware" is used herein in reference to both dishes and cutlery.

As used herein, the term "bleaching" refers to the treatment of a material (e.g., fabric, laundry, pulp, etc.) or surface for a sufficient length of time and under appropriate pH and temperature conditions to effect a brightening (i.e., whitening) and/or cleaning of the material. Examples of chemicals suitable for bleaching include but are not limited to $ClO_2$, $H_2O_2$, peracids, $NO_2$, etc.

As used herein, "wash performance" of a variant lipase refers to the contribution of a variant lipase to washing that provides additional cleaning performance to the detergent without the addition of the variant lipase to the composition. Wash performance is compared under relevant washing conditions.

The term "relevant washing conditions" is used herein to indicate the conditions, particularly washing temperature, time, washing mechanics, sud concentration, type of detergent and water hardness, actually used in households in a dish or laundry detergent market segment.

As used herein, the term "disinfecting" refers to the removal of contaminants from the surfaces, as well as the inhibition or killing of microbes on the surfaces of items. It is not intended that the present disclosure be limited to any particular surface, item, or contaminant(s) or microbes to be removed.

The "compact" form of the cleaning compositions herein is best reflected by density and, in terms of composition, by the amount of inorganic filler salt. Inorganic filler salts are conventional ingredients of detergent compositions in powder form. In conventional detergent compositions, the filler salts are present in substantial amounts, typically about 17 to about 35% by weight of the total composition. In contrast, in compact compositions, the filler salt is present in amounts not exceeding about 15% of the total composition. In some embodiments, the filler salt is present in amounts that do not exceed about 10%, or more preferably, about 5%, by weight of the composition. In some embodiments, the inorganic filler salts are selected from the alkali and alkaline-earth-metal salts of sulfates and chlorides. In some embodiments, a preferred filler salt is sodium sulfate.

As used herein, the terms "textile" or "textile material" refer to woven fabrics, as well as staple fibers and filaments suitable for conversion to or use as yarns, woven, knit, and non-woven fabrics. The term encompasses yarns made from natural, as well as synthetic (e.g., manufactured) fibers.

As used herein, the terms "purified" and "isolated" refer to the physical separation of a subject molecule, such as GeoT1 polypeptide, from other molecules, such as proteins, nucleic acids, lipids, media components, and the like. Once purified or isolated, a subject molecule may represent at least 50%, and even at least 60%, at least 70%, at least 80%, at least 85%, at least 90%, at least 95%, or more, of the total amount of material in a sample (wt/wt).

As used herein, a "polypeptide" refers to a molecule comprising a plurality of amino acids linked through peptide bonds. The terms "polypeptide," "peptide," and "protein" are used interchangeably. Proteins maybe optionally be modified (e.g., glycosylated, phosphorylated, acylated, farnesylated, prenylated, sulfonated, and the like) to add functionality. Where such amino acid sequences exhibit activity, they may be referred to as an "enzyme." The conventional one-letter or three-letter codes for amino acid residues are used, with amino acid sequences being presented in the standard amino-to-carboxy terminal orientation (i.e., N→C).

The terms "polynucleotide" encompasses DNA, RNA, heteroduplexes, and synthetic molecules capable of encoding a polypeptide. Nucleic acids may be single stranded or double stranded, and may be chemical modifications. The terms "nucleic acid" and "polynucleotide" are used interchangeably. Because the genetic code is degenerate, more than one codon may be used to encode a particular amino acid, and the present compositions and methods encompass nucleotide sequences which encode a particular amino acid sequence. Unless otherwise indicated, nucleic acid sequences are presented in a 5'-to-3' orientation.

As used herein, the terms "wild-type" and "native" refer to polypeptides or polynucleotides that are found in nature.

The terms, "wild-type," "parental," or "reference," with respect to a polypeptide, refer to a naturally-occurring polypeptide that does not include a man-made substitution, insertion, or deletion at one or more amino acid positions. Similarly, the terms "wild-type," "parental," or "reference," with respect to a polynucleotide, refer to a naturally-occurring polynucleotide that does not include a man-made nucleoside change. However, note that a polynucleotide encoding a wild-type, parental, or reference polypeptide is not limited to a naturally-occurring polynucleotide, and encompasses any polynucleotide encoding the wild-type, parental, or reference polypeptide.

As used herein, a "variant polypeptide" refers to a polypeptide that is derived from a parent (or reference) polypeptide by the substitution, addition, or deletion, of one or more amino acids, typically by recombinant DNA techniques. Variant polypeptides may differ from a parent polypeptide by a small number of amino acid residues and may be defined by their level of primary amino acid sequence homology/identity with a parent polypeptide. Preferably, variant polypeptides have at least 70%, at least 75%, at least 80%, at least 85%, at least 90%, at least 91%, at least 92%, at least 93%, at least 94%, at least 95%, at least 96%, at least 97%, at least 98%, or even at least 99% amino acid sequence identity with a parent polypeptide.

Sequence identity may be determined using known programs such as BLAST, ALIGN, and CLUSTAL using standard parameters. (See, e.g., Altschul et al. (1990) *J. Mol. Biol.* 215:403-410; Henikoff et al. (1989) *Proc. Natl. Acad. Sci. USA* 89:10915; Karin et al. (1993) *Proc. Natl. Acad. Sci. USA* 90:5873; and Higgins et al. (1988) *Gene* 73:237-244). Software for performing BLAST analyses is publicly available through the National Center for Biotechnology Information. Also, databases may be searched using FASTA (Pearson et al. (1988) *Proc. Natl. Acad. Sci. USA* 85:2444-2448). One indication that two polypeptides are substantially identical is that the first polypeptide is immunologically cross-reactive with the second polypeptide. Typically, polypeptides that differ by conservative amino acid substitutions are immunologically cross-reactive. Thus, a polypeptide is substantially identical to a second polypeptide, for example, where the two peptides differ only by a conservative substitution.

As used herein, a "variant polynucleotide" encodes a variant polypeptide, has a specified degree of homology/identity with a parent polynucleotide, or hybridized under stringent conditions to a parent polynucleotide or the complement, thereof. Preferably, a variant polynucleotide has at least 70%, at least 75%, at least 80%, at least 85%, at least 90%, at least 91%, at least 92%, at least 93%, at least 94%, at least 95%, at least 96%, at least 97%, at least 98%, or even at least 99% nucleotide sequence identity with a parent polynucleotide. Methods for determining percent identity are known in the art and described immediately above.

The term "derived from" encompasses the terms "originated from," "obtained from," "obtainable from," "isolated from," and "created from," and generally indicates that one specified material find its origin in another specified material or has features that can be described with reference to the another specified material.

As used herein, the term "hybridization" refers to the process by which a strand of nucleic acid joins with a complementary strand through base pairing, as known in the art.

As used herein, the phrase "hybridization conditions" refers to the conditions under which hybridization reactions are conducted. These conditions are typically classified by degree of "stringency" of the conditions under which hybridization is measured. The degree of stringency can be based, for example, on the melting temperature (Tm) of the nucleic acid binding complex or probe. For example, "maximum stringency" typically occurs at about Tm-5° C. (5° below the Tm of the probe); "high stringency" at about 5-10° below the Tm; "intermediate stringency" at about 10-20° below the Tm of the probe; and "low stringency" at about 20-25° below the Tm. Alternatively, or in addition, hybridization conditions can be based upon the salt or ionic strength conditions of hybridization and/or one or more stringency washes, e.g.: 6×SSC=very low stringency; 3×SSC=low to medium stringency; 1×SSC=medium stringency; and 0.5×SSC=high stringency. Functionally, maximum stringency conditions may be used to identify nucleic acid sequences having strict identity or near-strict identity with the hybridization probe; while high stringency conditions are used to identify nucleic acid sequences having about 80% or more sequence identity with the probe. For applications requiring high selectivity, it is typically desirable to use relatively stringent conditions to form the hybrids (e.g., relatively low salt and/or high temperature conditions are used). As used herein, stringent conditions are defined as 50° C. and 0.2×SSC (1×SSC=0.15 M NaCl, 0.015 M sodium citrate, pH 7.0).

The phrases "substantially similar" and "substantially identical" in the context of at least two nucleic acids or polypeptides means that a polynucleotide or polypeptide comprises a sequence that has at least about 90%, at least about 91%, at least about 92%, at least about 93%, at least about 94%, at least about 95%, at least about 96%, at least about 97%, at least about 98%, or even at least about 99% identical to a parent or reference sequence, or does not include amino acid substitutions, insertions, deletions, or modifications made only to circumvent the present description without adding functionality.

As used herein, an "expression vector" refers to a DNA construct containing a DNA sequence that encodes a specified polypeptide and is operably linked to a suitable control sequence capable of effecting the expression of the polypeptides in a suitable host. Such control sequences include a promoter to effect transcription, an optional operator sequence to control such transcription, a sequence encoding suitable mRNA ribosome binding sites and sequences which control termination of transcription and translation. The vector may be a plasmid, a phage particle, or simply a potential genomic insert. Once transformed into a suitable host, the vector may replicate and function independently of the host genome, or may, in some instances, integrate into the genome itself.

The term "recombinant," refers to genetic material (i.e., nucleic acids, the polypeptides they encode, and vectors and cells comprising such polynucleotides) that has been modified to alter its sequence or expression characteristics, such as by mutating the coding sequence to produce an altered polypeptide, fusing the coding sequence to that of another gene, placing a gene under the control of a different promoter, expressing a gene in a heterologous organism, expressing a gene at a decreased or elevated levels, expressing a gene conditionally or constitutively in manner different from its natural expression profile, and the like. Generally recombinant nucleic acids, polypeptides, and cells based thereon, have been manipulated by man such that they are not identical to related nucleic acids, polypeptides, and cells found in nature.

A "signal sequence" refers to a sequence of amino acids bound to the N-terminal portion of a polypeptide, and which facilitates the secretion of the mature form of the protein from the cell. The mature form of the extracellular protein lacks the signal sequence which is cleaved off during the secretion process.

The term "selective marker" or "selectable marker" refers to a gene capable of expression in a host cell that allows for ease of selection of those hosts containing an introduced nucleic acid or vector. Examples of selectable markers include but are not limited to antimicrobial substances (e.g., hygromycin, bleomycin, or chloramphenicol) and/or genes that confer a metabolic advantage, such as a nutritional advantage, on the host cell.

The term "regulatory element" as used herein refers to a genetic element that controls some aspect of the expression of nucleic acid sequences. For example, a promoter is a regulatory element which facilitates the initiation of transcription of an operably linked coding region. Additional regulatory elements include splicing signals, polyadenylation signals and termination signals.

As used herein, "host cells" are generally prokaryotic or eukaryotic hosts which are transformed or transfected with vectors constructed using recombinant DNA techniques known in the art. Transformed host cells are capable of either replicating vectors encoding the protein variants or expressing the desired protein variant. In the case of vectors which encode the pre- or prepro-form of the protein variant, such variants, when expressed, are typically secreted from the host cell into the host cell medium.

The term "introduced" in the context of inserting a nucleic acid sequence into a cell, means transformation, transduction or transfection. Means of transformation include protoplast transformation, calcium chloride precipitation, electroporation, naked DNA and the like as known in the art. (See, Chang and Cohen (1979) *Mol. Gen. Genet.*, 168:111-115; Smith et al. (1986) *Appl. Env. Microbiol.*, 51:634; and the review article by Ferrari et al., in Harwood, *Bacillus*, Plenum Publishing Corporation, pp. 57-72, 1989).

The terms "selectable marker" or "selectable gene product" as used herein refer to the use of a gene which encodes an enzymatic activity that confers resistance to an antibiotic or drug upon the cell in which the selectable marker is expressed.

Other technical and scientific terms have the same meaning as commonly understood by one of ordinary skill in the art to which this disclosure pertains (see, e.g., Singleton and Sainsbury, *Dictionary of Microbiology and Molecular Biology*, 2d Ed., John Wiley and Sons, NY (1994); and Hale and Marham, *The Harper Collins Dictionary of Biology*, Harper Perennial, NY (1991).

The singular terms "a," "an," and "the" include the plural reference unless the context clearly indicates otherwise.

Headings are provided for convenience and should not be construed as limitations. The description included under one heading may apply to the specification as a whole.

III. GeoT1 Polypeptides and Polynucleotides

A. GeoT1 Polypeptides

In one aspect, the present compositions and methods provide a recombinant GeoT1 polypeptide or a variant thereof. An exemplary GeoT1 polypeptide was isolated from *Geobacillus stearothermophilus* strain T1 (GENBANK Accession No. JC8061). The mature GeoT1 polypeptide has the amino acid sequence of SEQ ID NO: 4. Similarly, substantially identical GeoT1 polypeptides may occur in nature, e.g., in other strains or isolates of *G. stearothermophilus*. The disclosed GeoT1 polypeptides may also be fused to the carboxy-terminus of the catalytic domain of a bacterial cellulase. For example the bacterial cellulase may be derived from a *Bacillus* strain deposited as CBS 670.93 (referred to as BCE103) with the Central Bureau voor Schimmelcultures, Baam, The Netherlands). The GeoT1 polypeptide may also be connected to the BCE103 cellulase by a cleavable linker. These and other recombinant GeoT1 polypeptides are encompassed by the present compositions and methods.

In some embodiments, the recombinant GeoT1 polypeptide is a variant GeoT1 polypeptide having a specified degree of amino acid sequence homology to the exemplified GeoT1 polypeptide, e.g., at least 70%, at least 75%, at least 80%, at least 85%, at least 90%, at least 91%, at least 92%, at least 93%, at least 94%, at least 95%, at least 96%, at least 97%, at least 98%, or even at least 99% sequence homology to the amino acid sequence of SEQ ID NO: 4. Homology can be determined by amino acid sequence alignment, e.g., using a program such as BLAST, ALIGN, or CLUSTAL, as described herein.

In some embodiments, the recombinant GeoT1 polypeptide includes substitutions that do not substantially affect the structure and/or function of the polypeptide. Exemplary substitutions are conservative mutations, as summarized in Table I.

TABLE I

Amino Acid Substitutions

| Original Residue | Code | Acceptable Substitutions |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S—Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, beta-Ala, Acp |
| Isoleucine | I | D-Ile, Val, D-Val, Leu, D-Leu, Met, D-Met |
| Leucine | L | D-Leu, Val, D-Val, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S—Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-I-thioazolidine-4-carboxylic acid, D-or L-1-oxazolidine-4- carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

Substitutions involving naturally occurring amino acids are generally made by mutating a nucleic acid encoding a recombinant GeoT1 polypeptide, and then expressing the variant polypeptide in an organism. Substitutions involving non-naturally occurring amino acids or chemical modifications to amino acids are generally made by chemically modifying a recombinant GeoT1 polypeptide after it has been synthesized by an organism.

In some embodiments, variant recombinant GeoT1 polypeptides are substantially identical to SEQ ID NO: 4, meaning that they do not include amino acid substitutions, insertions, or deletions that do not significantly affect the structure, function or expression of the polypeptide. Such variant recombinant GeoT1 polypeptides include those designed only to circumvent the present description.

In some embodiments, the recombinant GeoT1 polypeptide (including a variant, thereof) has carboxylic ester hydrolase activity, which includes lipase, esterase, transesterase, and/or acyltransferase activity. Carboxylic ester hydrolase activity can be determined and measured using the assays described herein, or by other assays known in the art. In some embodiments, the recombinant GeoT1 polypeptide has activity in the presence of a detergent composition.

GeoT1 polypeptides include fragments of "full-length" GeoT1 polypeptides that retain carboxylic ester hydrolase activity. Such fragments preferably retain the active site of the full-length polypeptides but may have deletions of non-critical amino acid residues. The activity of fragments can readily be determined using the assays described, herein, or by other assays known in the art. In some embodiments, the fragments of GeoT1 polypeptides retain carboxylic ester hydrolase activity in the presence of a detergent composition.

In some embodiments, the GeoT1 polypeptide is fused to a signal peptide for directing the extracellular secretion of the GeoT1 polypeptide. In preferred embodiments, the lipase is fused to the carboxy-terminus of the catalytic domain of a bacterial cellulase. In a particularly preferred embodiment, the bacterial cellulase is derived from a *Bacillus* strain deposited as CBS 670.93 (referred to as BCE103) with the Central Bureau voor Schimmelcultures, Baam, The Netherlands). In other embodiments, the GeoT1 polypeptide may be connected to the BCE103 cellulase by a cleavable linker. An exemplary polypeptide sequence encoding a GeoT1 polypeptide fused to the catalytic domain of BCE103 cellulase is SEQ ID NO: 5.

In some embodiments, the GeoT1 polypeptide is expressed in a heterologous organism, i.e., an organism other than *Geobacillus stearothermophilus*. Exemplary heterologous organisms are Gram(+) bacteria such as *Bacillus licheniformis, Bacillus subtilis, Bacillus lentus, Bacillus brevis, Bacillus alkalophilus, Bacillus amyloliquefaciens, Bacillus coagulans, Bacillus circulans, Bacillus lautus, Bacillus megaterium, Bacillus thuringiensis, Streptomyces lividans*, or *Streptomyces murinus*; Gram(−) bacteria such as *E. coli*; yeast such as *Saccharomyces* spp. or *Schizosaccharomyces* spp., e.g. *Saccharomyces cerevisiae*; and filamentous fungi such as *Aspergillus* spp., e.g., *Aspergillus oryzae* or *Aspergillus niger*, and *Trichoderma reesei*. Methods from transforming nucleic acids into these organisms are well known in the art. A suitable procedure for transformation of *Aspergillus* host cells is described in EP 238 023.

In particular embodiments, the GeoT1 polypeptide is expressed in a heterologous organism as a secreted polypeptide, in which case, the compositions and method encompass a method for expressing a GeoT1 polypeptide as a secreted polypeptide in a heterologous organism.

B. GeoT1 Polynucleotides

Another aspect of the compositions and methods is a polynucleotide that encodes a GeoT1 polypeptide (including variants and fragments, thereof), provided in the context of an expression vector for directing the expression of a GeoT1 polypeptide in a heterologous organism, such as those identified, herein. The polynucleotide that encodes a GeoT1 polypeptide may be operably-linked to regulatory elements (e.g., a promoter, terminator, enhancer, and the like) to assist in expressing the encoded polypeptides.

An exemplary polynucleotide sequence encoding a GeoT1 polypeptide has the nucleotide sequence of SEQ ID NO: 1. Similar, including substantially identical, polynucleotides encoding GeoT1 polypeptides and variants may occur in nature, e.g., in other strains or isolates of *Geobacillus stearothermophilus*. In view of the degeneracy of the genetic code, it will be appreciated that polynucleotides having different nucleotide sequences may encode the same GeoT1 polypeptides, variants, or fragments.

In some embodiments, polynucleotides encoding GeoT1 polypeptides have a specified degree of amino acid sequence homology to the exemplified polynucleotide encoding a GeoT1 polypeptide, e.g., at least 70%, at least 75%, at least 80%, at least 85%, at least 90%, at least 91%, at least 92%, at least 93%, at least 94%, at least 95%, at least 96%, at least 97%, at least 98%, or even at least 99% sequence homology to the amino acid sequence of SEQ ID NO: 4. Homology can be determined by amino acid sequence alignment, e.g., using a program such as BLAST, ALIGN, or CLUSTAL™, as described herein.

In some embodiments, the polynucleotide that encodes a GeoT1 polypeptide is fused in frame behind (i.e., downstream of) a coding sequence for a signal peptide for directing the extracellular secretion of a GeoT1 polypeptide. Heterologous signal sequences include those from bacterial cellulase genes. In some embodiments, the bacterial cellulase is derived from a *Bacillus* strain deposited as CBS 670.93 (referred to as BCE103) with the Central Bureau voor Schimmelcultures, Baam, The Netherlands). The polynucleotide may also be fused to a coding sequence for a different polypeptide, thereby encoding a chimeric polypeptide. An exemplary polynucleotide sequence encoding a GeoT1 polypeptide fused to the catalytic domain of BCE103 cellulase is SEQ ID NO: 3. Expression vectors may be provided in a heterologous host cell suitable for expressing a GeoT1 polypeptide, or suitable for propagating the expression vector prior to introducing it into a suitable host cell.

In some embodiments, polynucleotides encoding GeoT1 polypeptides hybridize to the exemplary polynucleotide of SEQ ID NO: 1, SEQ ID NO: 2, or SEQ ID NO: 3 (or the complement, thereof) under specified hybridization conditions. Exemplary conditions are stringent condition and highly stringent conditions, which are described, herein.

GeoT1 polynucleotides may be naturally occurring or synthetic (i.e., man-made), and may be codon-optimized for expression in a different host, mutated to introduce cloning sites, or otherwise altered to add functionality.

IV. Activities of GeoT1

The GeoT1 polypeptides disclosed herein have enzymatic activity over a broad range of pH conditions. In certain embodiments the disclosed GeoT1 polypeptides have enzymatic activity from about pH 4 to about pH 11.5. In preferred embodiments, GeoT1 polypeptide is active from about pH 8 to about pH 10. It should be noted that the pH values described herein may vary by ±0.2. For example a pH value of about 8 could vary from pH 7.8 to pH 8.2.

The GeoT1 polypeptides disclosed herein may have enzymatic activity over a wide range of temperatures, e.g., from 10° C. or lower to about 50° C. In certain embodiments, the optimum temperature range for GeoT1 polypeptide is from about 10° C. to about 20° C., from about 20° C. to about 30° C., from about 30° C. to about 40° C., or from about 40° C. to about 50° C. It should be noted that the temperature values described herein may vary by ±0.2° C. For example a temperature of about 10° C. could vary from 9.8° C. to 10.2° C.

As shown in Example 3, the activity of GeoT1 was highest using a C8 substrate, but activity was observed using C4 and C16 substrates. In contrast, the commercially produced lipase LIPOMAX™ (*Pseudomonas pseudoalcaligenes* lipase variant M21L, Genencor Int. Inc., Palo Alto, Calif. had a preference for C10 substrates, with activity falling off rapidly with smaller (e.g., C8) or larger (e.g., C16) substrates (not shown). Therefore, GeoT1 appears to be less selective that LIPOMAX™ for substrates of a particular length, while having a preference for substrates with a shorter chain length than LIPOMAX™. GeoT1 showed hydrolysis activity against an exemplary oily stain material, in the presence of detergent compositions both in solution (Example 4) and when the stain was present on fabric (Example 5).

V. Detergent Compositions Comprising a GeoT1 Polypeptide

An aspect of the compositions and methods disclosed herein is a detergent composition comprising a GeoT1 polypeptide or a BCE-GeoT1 fusion polypeptide (including variants or fragments, thereof) and methods for using such compositions in cleaning applications. Cleaning applications include, but are not limited to, laundry or textile cleaning, dishwashing (manual and automatic), stain pre-treatment, and the like. Particular applications are those where lipids are a component of the soils or stains to be removed. Detergent compositions typically include an effective amount of GeoT1 or a variant thereof, e.g., at least 0.0001 weight percent, from about 0.0001 to about 1, from about 0.001 to about 0.5, from about 0.01 to about 0.1 weight percent, or even from about 0.1 to about 1 weight percent, or more. Detergent compositions having a concentration from about 0.4 g/L to about 2.2 g/L, from about 0.4 g/L to about 2.0 g/L, from about 0.4 g/L to about 1.7 g/L, from about 0.4 g/L to about 1.5 g/L, from about 0.4 g/L to about 1 g/L, from about 0.4 g/L to about 0.8 g/L, or from about 0.4 g/L to about 0.5 g/L may be mixed with an effective amount of a GeoT1 polypeptide. The detergent composition may also be present at a concentration of about 0.4 ml/L to about 2.6 ml/L, from about 0.4 ml/L to about 2.0 ml/L, from about 0.4 ml/L to about 1.5 m/L, from about 0.4 ml/L to about 1 ml/L, from about 0.4 ml/L to about 0.8 ml/L, or from about 0.4 ml/L to about 0.5 ml/L.

Unless otherwise noted, all component or composition levels provided herein are made in reference to the active level of that component or composition, and are exclusive of impurities, for example, residual solvents or by-products, which may be present in commercially available sources. Enzyme components weights are based on total active protein. All percentages and ratios are calculated by weight unless otherwise indicated. All percentages and ratios are calculated based on the total composition unless otherwise indicated. In the exemplified detergent compositions, the enzymes levels are expressed by pure enzyme by weight of the total composition and unless otherwise specified, the detergent ingredients are expressed by weight of the total compositions.

In some embodiments, the detergent composition comprises one or more surfactants, which may be non-ionic, semi-polar, anionic, cationic, zwitterionic, or combinationalions and mixtures thereof. The surfactants are typically present at a level of from about 0.1% to 60% by weight. Exemplary surfactants include but are not limited to sodium dodecylbenzene sulfonate, C12-14 pareth-7, C12-15 pareth-7, C12-15 pareth sulfate, C14-15 pareth-4, sodium laureth sulfate (e.g., Steol CS-370), sodium hydrogenated cocoate, C12 ethoxylates (Alfonic 1012-6, Hetoxol LA7, Hetoxol LA4), sodium alkyl benzene sulfonates (e.g., Nacconol 90G), and combinations and mixtures thereof.

Anionic surfactants that may be used with the detergent compositions described herein include but are not limited to linear alkylbenzenesulfonate (LAS), alpha-olefinsulfonate (AOS), alkyl sulfate (fatty alcohol sulfate) (AS), alcohol ethoxysulfate (AEOS or AES), secondary alkanesulfonates (SAS), alpha-sulfo fatty acid methyl esters, alkyl- or alkenylsuccinic acid, or soap. It may also contain 0-40% of nonionic surfactant such as alcohol ethoxylate (AEO or AE), carboxylated alcohol ethoxylates, nonylphenol ethoxylate, alkylpolyglycoside, alkyldimethylamine oxide, ethoxylated fatty acid monoethanolamide, fatty acid monoethanolamide, polyhydroxy alkyl fatty acid amide (e.g., as described in WO 92/06154), and combinations and mixtures thereof.

Nonionic surfactants that may be used with the detergent compositions described herein include but are not limited to polyoxyethylene esters of fatty acids, polyoxyethylene sorbitan esters (e.g., TWEENs), polyoxyethylene alcohols, polyoxyethylene isoalcohols, polyoxyethylene ethers (e.g., TRITONs and BRIJ), polyoxyethylene esters, polyoxyethylenep-tert-octylphenols or octylphenyl-ethylene oxide condensates (e.g., NONIDET P40), ethylene oxide condensates with fatty alcohols (e.g., LUBROL), polyoxyethylene nonylphenols, polyalkylene glycols (SYNPERONIC F108), sugar-based surfactants (e.g., glycopyranosides, thioglycopyranosides), and combinations and mixtures thereof.

The detergent compositions disclosed herein may have mixtures that include but are not limited to 5-15% anionic surfactants, <5% nonionic surfactants, cationic surfactants, phosphonates, soap, enzymes, perfume, butylphenyl methylptopionate, geraniol, zeolite, polycarboxylates, hexyl cinnamal, limonene, cationic surfactants, citronellol, and benzisothiazolinone.

Detergent compositions may additionally include one or more detergent builders or builder systems, a complexing agent, a polymer, a bleaching system, a stabilizer, a foam booster, a suds suppressor, an anti-corrosion agent, a soil-suspending agent, an anti-soil redeposition agent, a dye, a bactericide, a hydrotope, a tarnish inhibitor, an optical brightener, a fabric conditioner, and a perfume. The detergent compositions may also include enzymes, including but not limited to proteases, amylases, cellulases, lipases, or additional carboxylic ester hydrolases. The pH of the detergent compositions should be neutral to basic, as described, herein.

In some embodiments incorporating at least one builder, the detergent compositions comprise at least about 1%, from about 3% to about 60% or even from about 5% to about 40% builder by weight of the cleaning composition. Builders may include, but are not limited to, the alkali metal, ammonium and alkanolammonium salts of polyphosphates, alkali metal silicates, alkaline earth and alkali metal carbonates, aluminosilicates, polycarboxylate compounds, ether hydroxypolycarboxylates, copolymers of maleic anhydride with ethylene or vinyl methyl ether, 1,3,5-trihydroxy benzene-2,4,6-trisulphonic acid, and carboxymethyloxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, citric acid, oxydisuccinic acid, polymaleic acid, benzene 1,3,5-tricarboxylic acid, carboxymethyloxysuccinic acid, and soluble salts thereof. Indeed, it is contemplated that any suitable builder will find use in various embodiments of the present disclosure.

In some embodiments, the builders form water-soluble hardness ion complexes (e.g., sequestering builders), such as citrates and polyphosphates (e.g., sodium tripolyphosphate and sodium tripolyphospate hexahydrate, potassium tripolyphosphate, and mixed sodium and potassium tripolyphosphate, etc.). It is contemplated that any suitable builder will find use in the present disclosure, including those known in the art (see e.g., EP 2 100 949).

As indicated herein, in some embodiments, the cleaning compositions described herein further comprise adjunct materials including, but not limited to, surfactants, builders, bleaches, bleach activators, bleach catalysts, other enzymes, enzyme stabilizing systems, chelants, optical brighteners, soil release polymers, dye transfer agents, dispersants, suds suppressors, dyes, perfumes, colorants, filler salts, hydrotropes, photoactivators, fluorescers, fabric conditioners, hydrolyzable surfactants, preservatives, anti-oxidants, anti-shrinkage agents, anti-wrinkle agents, germicides, fungicides, color speckles, silvercare, anti-tarnish and/or anti-corrosion agents, alkalinity sources, solubilizing agents, carriers, processing aids, pigments, and pH control agents (see e.g., U.S. Pat. Nos. 6,610,642, 6,605,458, 5,705,464, 5,710,115, 5,698,504, 5,695,679, 5,686,014 and 5,646,101, all of which are incorporated herein by reference). Embodiments of specific cleaning composition materials are exemplified in detail below. In embodiments in which the cleaning adjunct materials are not compatible with the GeoT1 variants in the cleaning compositions, then suitable methods of keeping the cleaning adjunct materials and the lipase(s) separated (i.e., not in contact with each other) until combination of the two components is appropriate are used. Such separation methods include any suitable method known in the art (e.g., gelcaps, encapsulation, tablets, physical separation, etc.).

The cleaning compositions described herein are advantageously employed for example, in laundry applications, hard surface cleaning, dishwashing applications, as well as cosmetic applications such as dentures, teeth, hair and skin. In addition, due to the unique advantages of increased effectiveness in lower temperature solutions, the GeoT1 polypeptides described herein are ideally suited for laundry applications. Furthermore, the GeoT1 enzymes may find use in granular and liquid compositions.

The GeoT1 polypeptides described herein may also find use cleaning in additive products. In some embodiments, low temperature solution cleaning applications find use. In some embodiments, the present disclosure provides cleaning additive products including at least one disclosed GeoT1 polypeptide is ideally suited for inclusion in a wash process when additional bleaching effectiveness is desired. Such instances include, but are not limited to low temperature solution cleaning applications. In some embodiments, the additive product is in its simplest form, one or more lipases. In some embodiments, the additive is packaged in dosage form for addition to a cleaning process. In some embodiments, the additive is packaged in dosage form for addition to a cleaning process where a source of peroxygen is employed and increased bleaching effectiveness is desired. Any suitable single dosage unit form finds use with the present disclosure, including but not limited to pills, tablets, gelcaps, or other single dosage units such as pre-measured powders or liquids. In some embodiments, filler(s) or carrier material(s) are included to increase the volume of such compositions. Suitable filler or carrier materials include, but are not limited to, various salts of sulfate, carbonate and silicate as well as talc, clay and the like. Suitable filler or carrier materials for liquid compositions include, but are not limited to water or low molecular weight primary and secondary alcohols including polyols and diols. Examples of such alcohols include, but are not limited to, methanol, ethanol, propanol and isopropanol. In some embodiments, the compositions contain from about 5% to about 90% of such materials. Acidic fillers find use to reduce pH. Alternatively, in some embodiments, the cleaning additive includes adjunct ingredients, as more fully described below.

The present cleaning compositions and cleaning additives require an effective amount of at least one of the GeoT1 polypeptides described herein, alone or in combination with other lipases and/or additional enzymes. The required level of enzyme is achieved by the addition of one or more disclosed GeoT1 polypeptide. Typically the present cleaning compositions will comprise at least about 0.0001 weight percent, from about 0.0001 to about 10, from about 0.001 to about 1, or even from about 0.01 to about 0.1 weight percent of at least one of the disclosed GeoT1 polypeptides.

The cleaning compositions herein are typically formulated such that, during use in aqueous cleaning operations, the wash water will have a pH of from about 5.0 to about 11.5 or even from about 7.5 to about 10.5. Liquid product formulations are typically formulated to have a neat pH from about 3.0 to about 9.0 or even from about 3 to about 5. Granular laundry products are typically formulated to have a pH from about 9 to about 11. Techniques for controlling pH at recommended usage levels include the use of buffers, alkalis, acids, etc., and are well known to those skilled in the art.

Suitable low pH cleaning compositions typically have a neat pH of from about 3 to about 5, and are typically free of surfactants that hydrolyze in such a pH environment. Such surfactants include sodium alkyl sulfate surfactants that comprise at least one ethylene oxide moiety or even from about 1 to about 16 moles of ethylene oxide. Such cleaning compositions typically comprise a sufficient amount of a pH modifier, such as sodium hydroxide, monoethanolamine or hydrochloric acid, to provide such cleaning composition with a neat pH of from about 3 to about 5. Such compositions typically comprise at least one acid stable enzyme. In some embodiments, the compositions are liquids, while in other embodiments, they are solids. The pH of such liquid compositions is typically measured as a neat pH. The pH of such solid compositions is measured as a 10% solids solution of said composition wherein the solvent is distilled water. In these embodiments, all pH measurements are taken at 20° C., unless otherwise indicated.

In some embodiments, when the GeoT1 polypeptide is employed in a granular composition or liquid, it is desirable for the GeoT1 polypeptide to be in the form of an encapsulated particle to protect the GeoT1 polypeptide from other components of the granular composition during storage. In addition, encapsulation is also a means of controlling the availability of the GeoT1 polypeptide during the cleaning process. In some embodiments, encapsulation enhances the performance of the GeoT1 polypeptide and/or additional enzymes. In this regard, the GeoT1 polypeptides of the present disclosure are encapsulated with any suitable encapsulating material known in the art. In some embodiments, the encapsulating material typically encapsulates at least part of the catalyst for the GeoT1 polypeptides described herein. Typically, the encapsulating material is water-soluble and/or water-dispersible. In some embodiments, the encapsulating material has a glass transition temperature (Tg) of 0° C. or higher. Glass transition temperature is described in more detail in the PCT application WO 97/11151. The encapsulating material is typically selected from consisting of carbohydrates, natural or synthetic gums, chitin, chitosan, cellulose and cellulose derivatives, silicates, phosphates, borates, polyvinyl alcohol, polyethylene glycol, paraffin waxes, and combinations thereof. When the encapsulating material is a carbohydrate, it is typically selected from monosaccharides, oligosaccharides, polysaccharides, and combinations thereof. In some typical embodiments, the encapsulating material is a starch (see e.g., EP 0 922 499; U.S. Pat. No. 4,977,252; U.S. Pat. No. 5,354,559, and U.S. Pat. No. 5,935,826). In some embodiments, the encapsulating material is a microsphere made from plastic such as thermoplastics, acrylonitrile, methacrylonitrile, polyacrylonitrile, polymethacrylonitrile and mixtures thereof; commercially available microspheres that find use include, but are not limited to those supplied by EXPANCEL® (Stockviksverken, Sweden), and PM 6545, PM 6550, PM 7220, PM 7228, EXTENDOSPHERES®, LUXSIL®, Q-CEL®, and SPHERICEL® (PQ Corp., Valley Forge, Pa.).

In using detergent compositions that include GeoT1 in cleaning applications, the fabrics, textiles, dishes, or other surfaces to be cleaned are incubated in the presence of the GeoT1 detergent composition for a time sufficient to allow GeoT1 to hydrolyze lipids present in soil or stains, and then typically rinsed with water or another aqueous solvent to remove the GeoT1 detergent composition along with hydrolyzed lipids.

As described herein, the GeoT1 polypeptides find particular use in the cleaning industry, including, but not limited to laundry and dish detergents. These applications place enzymes under various environmental stresses. The GeoT1 polypeptides may provide advantages over many currently used enzymes, due to their stability under various conditions.

Indeed, there are a variety of wash conditions including varying detergent formulations, wash water volumes, wash water temperatures, and lengths of wash time, to which lipases involved in washing are exposed. In addition, detergent formulations used in different geographical areas have different concentrations of their relevant components present in the wash water. For example, European detergents typically have about 4,500-5,000 ppm of detergent components in the wash water, while Japanese detergents typically have approximately 667 ppm of detergent components in the wash water. In North America, particularly the United States, detergents typically have about 975 ppm of detergent components present in the wash water.

A low detergent concentration system includes detergents where less than about 800 ppm of the detergent components are present in the wash water. Japanese detergents are typically considered low detergent concentration system as they have approximately 667 ppm of detergent components present in the wash water.

A medium detergent concentration includes detergents where between about 800 ppm and about 2,000 ppm of the detergent components are present in the wash water. North American detergents are generally considered to be medium detergent concentration systems as they have approximately 975 ppm of detergent components present in the wash water. Brazil typically has approximately 1,500 ppm of detergent components present in the wash water.

A high detergent concentration system includes detergents where greater than about 2,000 ppm of the detergent components are present in the wash water. European detergents are generally considered to be high detergent concentration systems as they have approximately 4,500-5,000 ppm of detergent components in the wash water.

Latin American detergents are generally high suds phosphate builder detergents and the range of detergents used in Latin America can fall in both the medium and high detergent concentrations as they range from 1,500 ppm to 6,000 ppm of detergent components in the wash water. As mentioned above, Brazil typically has approximately 1,500 ppm of detergent components present in the wash water. However, other high suds phosphate builder detergent geographies, not limited to other Latin American countries, may have high detergent concentration systems up to about 6,000 ppm of detergent components present in the wash water.

In light of the foregoing, it is evident that concentrations of detergent compositions in typical wash solutions throughout the world varies from less than about 800 ppm of detergent composition ("low detergent concentration geographies"), for example about 667 ppm in Japan, to between about 800 ppm to about 2,000 ppm ("medium detergent concentration geographies"), for example about 975 ppm in U.S. and about 1,500 ppm in Brazil, to greater than about 2,000 ppm ("high detergent concentration geographies"), for example about 4,500 ppm to about 5,000 ppm in Europe and about 6000 ppm in high suds phosphate builder geographies.

The concentrations of the typical wash solutions are determined empirically. For example, in the U.S., a typical washing machine holds a volume of about 64.4 L of wash solution. Accordingly, in order to obtain a concentration of about 975 ppm of detergent within the wash solution about 62.79 g of detergent composition must be added to the 64.4 L of wash solution. This amount is the typical amount measured into the wash water by the consumer using the measuring cup provided with the detergent.

As a further example, different geographies use different wash temperatures. The temperature of the wash water in Japan is typically less than that used in Europe. For example, the temperature of the wash water in North America and Japan is typically between about 10 and about 30° C. (e.g., about 20° C.), whereas the temperature of wash water in Europe is typically between about 30 and about 60° C. (e.g., about 40° C.). However, in the interest of saving energy, many consumers are switching to using cold water washing. In addition, in some further regions, cold water is typically used for laundry, as well as dish washing applications. In some embodiments, the "cold water washing" of the present disclosure utilizes washing at temperatures from about 10° C. to about 40° C., or from about 20° C. to about 30° C., or from about 15° C. to about 25° C., as well as all other combinations within the range of about 15° C. to about 35° C., and all ranges within 10° C. to 40° C.

As a further example, different geographies typically have different water hardness. Water hardness is usually described in terms of the grains per gallon mixed $Ca^{2+}/Mg^{2+}$. Hardness is a measure of the amount of calcium ($Ca^{2+}$) and magnesium ($Mg^{2+}$) in the water. Most water in the United States is hard, but the degree of hardness varies. Moderately hard (60-120 ppm) to hard (121-181 ppm) water has 60 to 181 parts per million (parts per million converted to grains per U.S. gallon is ppm # divided by 17.1 equals grains per gallon) of hardness minerals.

TABLE II

Water Hardness Levels

| Water | Grains per gallon | Parts per million |
|---|---|---|
| Soft | less than 1.0 | less than 17 |
| Slightly hard | 1.0 to 3.5 | 17 to 60 |
| Moderately hard | 3.5 to 7.0 | 60 to 120 |
| Hard | 7.0 to 10.5 | 120 to 180 |
| Very hard | greater than 10.5 | greater than 180 |

European water hardness is typically greater than about 10.5 (for example about 10.5 to about 20.0) grains per gallon mixed $Ca^{2+}/Mg^{2+}$ (e.g., about 15 grains per gallon mixed $Ca^{2+}/Mg^{2+}$). North American water hardness is typically greater than Japanese water hardness, but less than European water hardness. For example, North American water hardness can be between about 3 to about 10 grains, about 3 to about 8 grains or about 6 grains. Japanese water hardness is typically lower than North American water hardness, usually less than about 4, for example about 3 grains per gallon mixed $Ca^{2+}/Mg^{2+}$.

Accordingly, in some embodiments, the present disclosure provides GeoT1 polypeptides that show surprising wash performance in at least one set of wash conditions (e.g., water temperature, water hardness, and/or detergent concentration). In some embodiments, the GeoT1 polypeptides are comparable in wash performance to other lipases. In some embodiments, the GeoT1 polypeptides exhibit enhanced wash performance as compared to lipases currently commercially available. Thus, in some preferred embodiments, the GeoT1 polypeptides provided herein exhibit enhanced oxidative stability, enhanced thermal stability, enhanced cleaning capabilities under various conditions, and/or enhanced chelator stability. In addition, the GeoT1 polypeptides may find use in cleaning compositions that do not include detergents, again either alone or in combination with builders and stabilizers.

In some embodiments of the present disclosure, the cleaning compositions comprise at least one GeoT1 polypeptide of the present disclosure at a level from about 0.00001% to about 10% by weight of the composition and the balance (e.g., about 99.999% to about 90.0%) comprising cleaning adjunct materials by weight of composition. In other aspects of the present disclosure, the cleaning compositions comprises at least one GeoT1 polypeptide at a level of about 0.0001% to about 10%, about 0.001% to about 5%, about 0.001% to about 2%, about 0.005% to about 0.5% by weight of the composition and the balance of the cleaning composition (e.g., about 99.9999% to about 90.0%, about 99.999% to about 98%, about 99.995% to about 99.5% by weight) comprising cleaning adjunct materials.

In some embodiments, the cleaning compositions described herein comprise one or more additional detergent enzymes, which provide cleaning performance and/or fabric care and/or dishwashing benefits. Examples of suitable enzymes include, but are not limited to, hemicellulases, cellulases, peroxidases, proteases, xylanases, lipases, phospholipases, esterases, cutinases, pectinases, pectate lyases, mannanases, keratinases, reductases, oxidases, phenoloxidases, lipoxygenases, ligninases, pullulanases, tannases, pentosanases, malanases, β-glucanases, arabinosidases, hyaluronidase, chondroitinase, laccase, and amylases, or mixtures thereof. In some embodiments, a combination of enzymes is used (i.e., a "cocktail") comprising conventional applicable enzymes like protease, lipase, cutinase and/or cellulase in conjunction with amylase is used.

In addition to the GeoT1 polypeptides provided herein, any other suitable lipase finds use in the compositions of the present disclosure. Suitable lipases include, but are not limited to those of bacterial or fungal origin. Chemically or genetically modified mutants are encompassed by the present disclosure. Examples of useful lipases include *Humicola lanuginosa* lipase (See e.g., EP 258 068, and EP 305 216), *Rhizomucor miehei* lipase (see, e.g., EP 238 023), *Candida* lipase, such as *C. antarctica* lipase (e.g., the *C. antarctica* lipase A or B; see e.g., EP 214 761), *Pseudomonas* lipases such as *P. alcaligenes* lipase and *P. pseudoalcaligenes* lipase (see e.g., EP 218 272), *P. cepacia* lipase (see, e.g., EP 331 376), *P. stutzeri* lipase (see, e.g., GB 1,372,034), *P. fluorescens* lipase, *Bacillus* lipase (e.g., *B. subtilis* lipase; Dartois et al., Biochem. Biophys. Acta 1131:253-260, 1993); *B. stearothermophilus* lipase (see, e.g., JP 64/744992); and *B. pumilus* lipase (see, e.g., WO 91/16422).

Furthermore, a number of cloned lipases find use in some embodiments of the present disclosure, including but not limited to *Penicillium camembertii* lipase (see, Yamaguchi et al., Gene 103:61-67, 1991), *Geotricum candidum* lipase (see, Schimada et al., J. Biochem., 106:383-388, 1989), and various *Rhizopus* lipases such as *R. delemar* lipase (see, Hass et al., Gene 109:117-113, 1991), a *R. niveus* lipase (Kugimiya et al., Biosci. Biotech. Biochem. 56:716-719, 1992) and *R. oryzae* lipase.

Other types of lipolytic enzymes such as cutinases also find use in some embodiments of the present disclosure, including but not limited to the cutinase derived from *Pseudomonas mendocina* (see, WO 88/09367), and the cutinase derived from *Fusarium solani pisi* (see, WO 90/09446).

Additional suitable lipases include commercially available lipases such as M1 LIPASE™, LUMA FAST™, and LIPOMAX™ (Danisco US Inc., Genencor Division, Palo Alto, Calif., USA); LIPOLASE® and LIPOLASE® ULTRA (Novozymes, Copenhagen, Denmark); and LIPASE P™ "Amano" (Amano Pharmaceutical Co. Ltd., Japan).

In some embodiments of the present disclosure, the cleaning compositions of the present disclosure further comprise lipases at a level from about 0.00001% to about 10% of additional lipase by weight of the composition and the balance of cleaning adjunct materials by weight of composition. In other aspects of the present disclosure, the cleaning compositions of the present disclosure also comprise lipases at a level of about 0.0001% to about 10%, about 0.001% to about 5%, about 0.001% to about 2%, about 0.005% to about 0.5% lipase by weight of the composition.

In some embodiments of the present disclosure, any suitable protease may be used. Suitable proteases include those of animal, vegetable or microbial origin. In some embodiments, chemically or genetically modified mutants are included. In some embodiments, the protease is a serine protease, preferably an alkaline microbial protease or a trypsin-like protease. In some embodiments, the protease is a subtilisin protease, including any of the large number of engineered subtilisin proteases known in the art. Various proteases are described in WO95/23221, WO 92/21760, U.S. Pat. Publ. No. 2008/0090747, and U.S. Pat. Nos. 5,801,039, 5,340,735, 5,500,364, 5,855,625, U.S. Pat. Re. 34,606, U.S. Pat. Nos. 5,955,340, 5,700,676, 6,312,936, and 6,482,628, and various other patents. In some further embodiments, metalloproteases find use in the present disclosure, including but not limited to the neutral metalloprotease described in WO 07/044,993.

In some embodiments of the present disclosure, any suitable amylase may be used. In some embodiments, any amylase (e.g., alpha and/or beta) suitable for use in alkaline solutions also find use. Suitable amylases include, but are not limited to those of bacterial or fungal origin. Chemically or genetically modified mutants are included in some embodiments. Amylases that find use in the present disclosure, include, but are not limited to α-amylases obtained from *B. licheniformis* (see e.g., GB 1,296,839). Commercially available amylases that find use in the present disclosure include, but are not limited to DURAMYL®, TERMAMYL®, FUNGAMYL®, STAINZYME®, STAINZYME PLUS®, STAINZYME ULTRA®, and BAN™ (Novozymes), as well as POWERASE™, RAPIDASE® and MAXAMYL® P (Genencor).

In some embodiments of the present disclosure, the disclosed cleaning compositions of further comprise amylases at a level from about 0.00001% to about 10% of additional amylase by weight of the composition and the balance of cleaning adjunct materials by weight of composition. In other aspects of the present disclosure, the cleaning compositions also comprise amylases at a level of about 0.0001% to about 10%, about 0.001% to about 5%, about 0.001% to about 2%, about 0.005% to about 0.5% amylase by weight of the composition.

In some further embodiments, any suitable cellulase finds used in the cleaning compositions of the present disclosure. Suitable cellulases include, but are not limited to those of bacterial or fungal origin. Chemically or genetically modified mutants are included in some embodiments. Suitable cellulases include, but are not limited to *Humicola insolens* cellulases (see e.g., U.S. Pat. No. 4,435,307). Especially suitable cellulases are the cellulases having color care benefits (see e.g., EP 0 495 257). Commercially available cellulases that find use in the present include, but are not limited to CELLUZYME®, CAREZYME® (Novozymes), and KAC-500 (B)™ (Kao Corporation). In some embodiments, cellulases are incorporated as portions or fragments of mature wild-type or variant cellulases, wherein a portion of the N-terminus is deleted (see e.g., U.S. Pat. No. 5,874,276). In some embodiments, the cleaning compositions of the present disclosure further comprise cellulases at a level from about 0.00001% to about 10% of additional cellulase by weight of the composition and the balance of cleaning adjunct materials by weight of composition. In other aspects of the present disclosure, the cleaning compositions also comprise cellulases at a level of about 0.0001% to about 10%, about 0.001% to about 5%, about 0.001% to about 2%, about 0.005% to about 0.5% cellulase by weight of the composition.

Any mannanase suitable for use in detergent compositions also finds use in the present disclosure. Suitable mannanases include, but are not limited to those of bacterial or fungal origin. Chemically or genetically modified mutants are included in some embodiments. Various mannanases are known which find use in the present disclosure (see e.g., U.S. Pat. No. 6,566,114, U.S. Pat. No. 6,602,842, and U.S. Pat. No. 6,440,991, all of which are incorporated herein by reference). In some embodiments, the disclosed cleaning compositions further comprise mannanases at a level from about 0.00001% to about 10% of additional mannanase by weight of the composition and the balance of cleaning adjunct materials by weight of composition. In other aspects of the present disclosure, the cleaning compositions also comprise mannanases at a level of about 0.0001% to about 10%, about 0.001% to about 5%, about 0.001% to about 2%, about 0.005% to about 0.5% mannanase by weight of the composition.

In some embodiments, peroxidases are used in combination with hydrogen peroxide or a source thereof (e.g., a percarbonate, perborate or persulfate) in the compositions of the present disclosure. In some alternative embodiments, oxidases are used in combination with oxygen. Both types of enzymes are used for "solution bleaching" (i.e., to prevent transfer of a textile dye from a dyed fabric to another fabric when the fabrics are washed together in a wash liquor), preferably together with an enhancing agent (see e.g., WO 94/12621 and WO 95/01426). Suitable peroxidases/oxidases include, but are not limited to those of plant, bacterial or fungal origin. Chemically or genetically modified mutants are included in some embodiments. In some embodiments, the cleaning compositions of the present disclosure further comprise peroxidase and/or oxidase enzymes at a level from about 0.00001% to about 10% of additional peroxidase and/or oxidase by weight of the composition and the balance of cleaning adjunct materials by weight of composition. In other aspects of the present disclosure, the cleaning compositions also comprise, peroxidase and/or oxidase enzymes at a level of about 0.0001% to about 10%, about 0.001% to about 5%, about 0.001% to about 2%, about 0.005% to about 0.5% peroxidase and/or oxidase enzymes by weight of the composition.

In some embodiments, additional enzymes find use, including but not limited to perhydrolases (see e.g., WO 05/056782). In addition, in some particularly preferred embodiments, mixtures of the above mentioned enzymes are encompassed herein, in particular one or more additional protease, amylase, lipase, mannanase, and/or at least one cellulase. Indeed, it is contemplated that various mixtures of these enzymes will find use in the present disclosure. It is also contemplated that the varying levels of the GeoT1 polypeptide(s) and one or more additional enzymes may both independently range to about 10%, the balance of the cleaning composition being cleaning adjunct materials. The specific selection of cleaning adjunct materials are readily made by considering the surface, item, or fabric to be cleaned, and the desired form of the composition for the cleaning conditions during use (e.g., through the wash detergent use).

Examples of suitable cleaning adjunct materials include, but are not limited to, surfactants, builders, bleaches, bleach activators, bleach catalysts, other enzymes, enzyme stabilizing systems, chelants, optical brighteners, soil release polymers, dye transfer agents, dye transfer inhibiting agents, catalytic materials, hydrogen peroxide, sources of hydrogen peroxide, preformed peracis, polymeric dispersing agents, clay soil removal agents, structure elasticizing agents, dispersants, suds suppressors, dyes, perfumes, colorants, filler salts, hydrotropes, photoactivators, fluorescers, fabric conditioners, fabric softeners, carriers, hydrotropes, processing aids, solvents, pigments, hydrolyzable surfactants, preservatives, anti-oxidants, anti-shrinkage agents, anti-wrinkle agents, germicides, fungicides, color speckles, silvercare, anti-tarnish and/or anti-corrosion agents, alkalinity sources, solubilizing agents, carriers, processing aids, pigments, and pH control agents (see e.g., U.S. Pat. Nos. 6,610,642, 6,605,458, 5,705,464, 5,710,115, 5,698,504, 5,695,679, 5,686,014 and 5,646,101, all of which are incorporated herein by reference). Embodiments of specific cleaning composition materials are exemplified in detail below. In embodiments in which the cleaning adjunct materials are not compatible with the disclosed GeoT1 polypeptides in the cleaning compositions, then suitable methods of keeping the cleaning adjunct materials and the lipase(s) separated (i.e., not in contact with each other) until combination of the two components is appropriate are used. Such separation methods include any suitable method known in the art (e.g., gelcaps, encapsulation, tablets, physical separation, etc.).

In some preferred embodiments, an effective amount of one or more GeoT1 polypeptide(s) provided herein are included in compositions useful for cleaning a variety of surfaces in need of stain removal. Such cleaning compositions include cleaning compositions for such applications as cleaning hard surfaces, fabrics, and dishes. Indeed, in some embodiments, the present disclosure provides fabric cleaning compositions, while in other embodiments, the present disclosure provides non-fabric cleaning compositions. Notably, the present disclosure also provides cleaning compositions suitable for personal care, including oral care (including dentrifices, toothpastes, mouthwashes, etc., as well as denture cleaning compositions), skin, and hair cleaning compositions. It is intended that the present disclosure encompass detergent compositions in any form (i.e., liquid, granular, bar, semi-solid, gels, emulsions, tablets, capsules, etc.).

By way of example, several cleaning compositions wherein the disclosed GeoT1 polypeptides find use are described in greater detail below. In some embodiments in which the disclosed cleaning compositions are formulated as compositions suitable for use in laundry machine washing method(s), the compositions of the present disclosure preferably contain at least one surfactant and at least one builder compound, as well as one or more cleaning adjunct materials preferably selected from organic polymeric compounds, bleaching agents, additional enzymes, suds suppressors, dispersants, lime-soap dispersants, soil suspension and anti-redeposition agents and corrosion inhibitors. In some embodiments, laundry compositions also contain softening agents (i.e., as additional cleaning adjunct materials). The compositions of the present disclosure also find use detergent additive products in solid or liquid form. Such additive products are intended to supplement and/or boost the performance of conventional detergent compositions and can be added at any stage of the cleaning process. In some embodiments, the density of the laundry detergent compositions herein ranges from about 400 to about 1200 g/liter, while in other embodiments, it ranges from about 500 to about 950 g/liter of composition measured at 20° C.

In embodiments formulated as compositions for use in manual dishwashing methods, the compositions of the disclosure preferably contain at least one surfactant and preferably at least one additional cleaning adjunct material selected from organic polymeric compounds, suds enhancing agents, group II metal ions, solvents, hydrotropes, and additional enzymes.

In some embodiments, various cleaning compositions such as those provided in U.S. Pat. No. 6,605,458, find use with the GeoT1 polypeptides of the present disclosure. Thus, in some embodiments, the compositions comprising at least one GeoT1 polypeptide of the present disclosure is a compact granular fabric cleaning composition, while in other embodiments, the composition is a granular fabric cleaning composition useful in the laundering of colored fabrics, in further embodiments, the composition is a granular fabric cleaning composition which provides softening through the wash capacity, in additional embodiments, the composition is a heavy duty liquid fabric cleaning composition. In some embodiments, the compositions comprising at least one GeoT1 polypeptide of the present disclosure are fabric cleaning compositions such as those described in U.S. Pat. Nos. 6,610,642 and 6,376,450. In addition, the GeoT1 polypeptides of the present disclosure find use in granular laundry detergent compositions of particular utility under European or Japanese washing conditions (see e.g., U.S. Pat. No. 6,610,642).

In some alternative embodiments, the present disclosure provides hard surface cleaning compositions comprising at least one GeoT1 polypeptide provided herein. Thus, in some embodiments, the compositions comprising at least one GeoT1 polypeptide of the present disclosure is a hard surface cleaning composition such as those described in U.S. Pat. Nos. 6,610,642, 6,376,450, and 6,376,450.

In yet further embodiments, the present disclosure provides dishwashing compositions comprising at least one GeoT1 polypeptide provided herein. Thus, in some embodiments, the compositions comprising at least one GeoT1 polypeptide of the present disclosure is a hard surface cleaning composition such as those in U.S. Pat. Nos. 6,610,642 and 6,376,450. In some still further embodiments, the present disclosure provides dishwashing compositions comprising at least one GeoT1 polypeptide provided herein. In some further embodiments, the compositions comprising at least one GeoT1 polypeptide of the present disclosure comprise oral care compositions such as those in U.S. Pat. Nos. 6,376,450, and 6,376,450. The formulations and descriptions of the compounds and cleaning adjunct materials contained in the aforementioned U.S. Pat. Nos. 6,376,450; 6,605,458; 6,605,458; and 6,610,642, find use with the GeoT1 polypeptides provided herein.

The cleaning compositions of the present disclosure are formulated into any suitable form and prepared by any process chosen by the formulator, non-limiting examples of which are described in U.S. Pat. Nos. 5,879,584; 5,691,297; 5,574,005; 5,569,645; 5,565,422; 5,516,448; 5,489,392; and 5,486,303, all of which are incorporated herein by reference. When a low pH cleaning composition is desired, the pH of such composition is adjusted via the addition of a material such as monoethanolamine or an acidic material such as HCl.

While not essential for the purposes of the present disclosure, the non-limiting list of adjuncts illustrated hereinafter are suitable for use in the instant cleaning compositions. In some embodiments, these adjuncts are incorporated for example, to assist or enhance cleaning performance, for treatment of the substrate to be cleaned, or to modify the aesthetics of the cleaning composition as is the case with perfumes, colorants, dyes or the like. It is understood that such adjuncts are in addition to the GeoT1 polypeptides of the present disclosure. The precise nature of these additional components, and levels of incorporation thereof, will depend on the physical form of the composition and the nature of the cleaning operation for which it is to be used. Suitable adjunct materials include, but are not limited to, surfactants, builders, chelating agents, dye transfer inhibiting agents, deposition aids, dispersants, additional enzymes, and enzyme stabilizers, catalytic materials, bleach activators, bleach boosters, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, processing aids and/or pigments. In addition to the disclosure below, suitable examples of such other adjuncts and levels of use are found in U.S. Pat. Nos. 5,576, 282; 6,306,812; and 6,326,348, incorporated by reference. The aforementioned adjunct ingredients may constitute the balance of the cleaning compositions of the present disclosure.

In some embodiments, the cleaning compositions according to the present disclosure comprise at least one surfactant and/or a surfactant system wherein the surfactant is selected from nonionic surfactants, anionic surfactants, cationic surfactants, ampholytic surfactants, zwitterionic surfactants, semi-polar nonionic surfactants and mixtures thereof. In some low pH cleaning composition embodiments (e.g., compositions having a neat pH of from about 3 to about 5), the composition typically does not contain alkyl ethoxylated sulfate, as it is believed that such surfactant may be hydrolyzed by such compositions the acidic contents. In some embodiments, the surfactant is present at a level of from about 0.1% to about 60%, while in alternative embodiments the level is from about 1% to about 50%, while in still further embodiments the level is from about 5% to about 40%, by weight of the cleaning composition.

In some embodiments, the cleaning compositions of the present disclosure contain at least one chelating agent. Suitable chelating agents may include, but are not limited to copper, iron and/or manganese chelating agents and mixtures thereof. In embodiments in which at least one chelating agent is used, the cleaning compositions of the present disclosure comprise from about 0.1% to about 15% or even from about 3.0% to about 10% chelating agent by weight of the subject cleaning composition.

In some still further embodiments, the cleaning compositions provided herein contain at least one deposition aid. Suitable deposition aids include, but are not limited to, polyethylene glycol, polypropylene glycol, polycarboxylate, soil release polymers such as polytelephthalic acid, clays such as kaolinite, montmorillonite, atapulgite, illite, bentonite, halloysite, and mixtures thereof.

As indicated herein, in some embodiments, anti-redeposition agents find use in some embodiments of the present disclosure. In some preferred embodiments, non-ionic surfactants find use. For example, in automatic dishwashing embodiments, non-ionic surfactants find use for surface modification purposes, in particular for sheeting, to avoid filming and spotting and to improve shine. These non-ionic surfactants also find use in preventing the re-deposition of soils. In some preferred embodiments, the anti-redeposition agent is a non-ionic surfactant as known in the art (see e.g., EP 2 100 949).

In some embodiments, the cleaning compositions of the present disclosure include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. In embodiments in which at least one dye transfer inhibiting agent is used, the cleaning compositions of the present disclosure comprise from about 0.0001% to about 10%, from about 0.01% to about 5%, or even from about 0.1% to about 3% by weight of the cleaning composition.

In some embodiments, silicates are included within the compositions of the present disclosure. In some such embodiments, sodium silicates (e.g., sodium disilicate, sodium metasilicate, and crystalline phyllosilicates) find use. In some embodiments, silicates are present at a level of from about 1% to about 20%. In some preferred embodiments, silicates are present at a level of from about 5% to about 15% by weight of the composition.

In some still additional embodiments, the cleaning compositions of the present disclosure also contain dispersants. Suitable water-soluble organic materials include, but are not limited to the homo- or co-polymeric acids or their salts, in which the polycarboxylic acid comprises at least two carboxyl radicals separated from each other by not more than two carbon atoms.

In some further embodiments, the enzymes used in the cleaning compositions are stabilized any suitable technique. In some embodiments, the enzymes employed herein are stabilized by the presence of water-soluble sources of calcium and/or magnesium ions in the finished compositions that provide such ions to the enzymes. In some embodiments, the enzyme stabilizers include oligosaccharides, polysaccharides, and inorganic divalent metal salts, including alkaline earth metals, such as calcium salts. It is contemplated that various techniques for enzyme stabilization will find use in the present disclosure. For example, in some embodiments, the enzymes employed herein are stabilized by the presence of water-soluble sources of zinc (II), calcium (II) and/or magnesium (II) ions in the finished compositions that provide such ions to the enzymes, as well as other metal ions (e.g., barium (II), scandium (II), iron (II), manganese (II), aluminum (III), Tin (II), cobalt (II), copper (II), nickel (II), and oxovanadium (IV). Chlorides and sulfates also find use in some embodiments of the present disclosure. Examples of suitable oligosaccharides and polysaccharides (e.g., dextrins) are known in the art (see, e.g., WO 07/145,964). In some embodiments, reversible protease inhibitors also find use, such as boron-containing compounds (e.g., borate, 4-formyl phenyl boronic acid) and/or a tripeptide aldehyde find use to further improve stability, as desired.

In some embodiments, bleaches, bleach activators and/or bleach catalysts are present in the compositions of the present disclosure. In some embodiments, the cleaning compositions of the present disclosure comprise inorganic and/or organic bleaching compound(s). Inorganic bleaches may include, but are not limited to perhydrate salts (e.g., perborate, percarbonate, perphosphate, persulfate, and persilicate salts). In some embodiments, inorganic perhydrate salts are alkali metal salts. In some embodiments, inorganic perhydrate salts are included as the crystalline solid, without additional protection, although in some other embodiments, the salt is coated. Any suitable salt known in the art finds use in the present disclosure (see, e.g., EP 2 100 949).

In some embodiments, bleach activators are used in the compositions of the present disclosure. Bleach activators are typically organic peracid precursors that enhance the bleaching action in the course of cleaning at temperatures of 60° C. and below. Bleach activators suitable for use herein include compounds which, under perhydrolysis conditions, give aliphaic peroxoycarboxylic acids having preferably from about 1 to about 10 carbon atoms, in particular from about 2 to about 4 carbon atoms, and/or optionally substituted perbenzoic acid. Additional bleach activators are known in the art and find use in the present disclosure (see, e.g., EP 2 100 949).

In addition, in some embodiments and as further described herein, the cleaning compositions of the present disclosure further comprise at least one bleach catalyst. In some embodiments, the manganese triazacyclononane and related complexes find use, as well as cobalt, copper, manganese, and iron complexes. Additional bleach catalysts find use in the present disclosure (see, e.g., U.S. Pat. Nos. 4,246,612, 5,227,084, 4,810,410, WO 99/06521, and EP 2 100 949).

In some embodiments, the cleaning compositions of the present disclosure contain one or more catalytic metal complexes. In some embodiments, a metal-containing bleach catalyst finds use. In some preferred embodiments, the metal bleach catalyst comprises a catalyst system comprising a transition metal cation of defined bleach catalytic activity, (e.g., copper, iron, titanium, ruthenium, tungsten, molybdenum, or manganese cations), an auxiliary metal cation having little or no bleach catalytic activity (e.g., zinc or aluminum cations), and a sequestrate having defined stability constants for the catalytic and auxiliary metal cations, particularly ethylenediaminetetraacetic acid, ethylenediaminetetra (methylenephosphonic acid) and water-soluble salts thereof are used (see, e.g., U.S. Pat. No. 4,430,243). In some embodiments, the cleaning compositions of the present disclosure are catalyzed by means of a manganese compound. Such compounds and levels of use are well known in the art (see, e.g., U.S. Pat. No. 5,576,282). In additional embodiments, cobalt bleach catalysts find use in the cleaning compositions of the present disclosure. Various cobalt bleach catalysts are known in the art (see, e.g., U.S. Pat. Nos. 5,597,936 and 5,595,967) and are readily prepared by known procedures.

In some additional embodiments, the cleaning compositions of the present disclosure include a transition metal complex of a macropolycyclic rigid ligand (MRL). As a practical matter, and not by way of limitation, in some embodiments, the compositions and cleaning processes provided by the present disclosure are adjusted to provide on the order of at least one part per hundred million of the active MRL species in the aqueous washing medium, and in some preferred embodiments, provide from about 0.005 ppm to about 25 ppm, more preferably from about 0.05 ppm to about 10 ppm, and most preferably from about 0.1 ppm to about 5 ppm, of the MRL in the wash liquor.

In some embodiments, preferred transition-metals in the instant transition-metal bleach catalyst include, but are not limited to manganese, iron and chromium. Preferred MRLs also include, but are not limited to special ultra-rigid ligands that are cross-bridged (e.g., 5,12-diethyl-1,5,8,12-tetraazabicyclo[6.6.2]hexadecane). Suitable transition metal MRLs are readily prepared by known procedures (see, e.g., WO 2000/32601, and U.S. Pat. No. 6,225,464).

In some embodiments, the cleaning compositions of the present disclosure comprise metal care agents. Metal care agents find use in preventing and/or reducing the tarnishing, corrosion, and/or oxidation of metals, including aluminum, stainless steel, and non-ferrous metals (e.g., silver and copper). Suitable metal care agents include those described in EP 2 100 949, WO 9426860 and WO 94/26859). In some embodiments, the metal care agent is a zinc salt. In some further embodiments, the cleaning compositions of the present disclosure comprise from about 0.1% to about 5% by weight of one or more metal care agent.

As indicated above, the cleaning compositions of the present disclosure are formulated into any suitable form and prepared by any process chosen by the formulator, non-limiting examples of which are described in U.S. Pat. Nos. 5,879,584; 5,691,297; 5,574,005; 5,569,645; 5,516,448; 5,489,392; and 5,486,303, all of which are incorporated herein by reference. In some embodiments in which a low pH cleaning composition is desired, the pH of such composition is adjusted via the addition of an acidic material such as HCl.

The cleaning compositions disclosed herein of find use in cleaning a situs (e.g., a surface, dishware, or fabric). Typically, at least a portion of the situs is contacted with an embodiment of the present cleaning composition, in neat form or diluted in a wash liquor, and then the situs is optionally washed and/or rinsed. For purposes of the present disclosure, "washing" includes but is not limited to, scrubbing, and mechanical agitation. In some embodiments, the cleaning compositions are typically employed at concentrations of from about 500 ppm to about 15,000 ppm in solution. When the wash solvent is water, the water temperature typically ranges from about 5° C. to about 90° C. and, when the situs comprises a fabric, the water to fabric mass ratio is typically from about 1:1 to about 30:1.

VI. GeoT1 Polypeptides as Chemical Reagents

The preference of GeoT1 for short-chain lipids makes the present polypeptides particularly useful for performing transesterification reactions involving C4-C16 substrates. Exemplary applications are the hydrolysis of milk fat; the synthesis of structured triglycerides, the synthesis and degradation of polymers, the formation of emulsifying agents and surfactants; the synthesis of ingredients for personal-care products, pharmaceuticals and agrochemicals, for making esters for use as perfumes and fragrances, for making biofuels and synthetic lubricants, for forming peracids, and for other uses in the oleochemical industry. Further uses for the above-described enzyme are described in U.S. Patent Pubs. 20070026106; 20060078648; and 20050196766, and in WO 2005/066347, which documents are incorporated by reference.

In general terms, a substrate and acceptor molecule are incubated in the presence of an GeoT1 polypeptide or variant thereof under conditions suitable for performing a transesterification reaction, followed by, optionally, isolating a product from the reaction. Alternatively, the conditions may in the context of a foodstuff and the product may become a component of the foodstuff without isolation.

Other aspects and embodiments of the present compositions and methods will apparent from the foregoing description and following examples.

EXAMPLES

The following examples are provided to demonstrate and illustrate certain preferred embodiments and aspects of the present disclosure and should not be construed as limiting.

In the experimental disclosure which follows, the following abbreviations apply: M (molar); mM (millimolar); µM (micromolar); nM (nanomolar); mol (moles); mmol (millimoles); µmol (micromoles); nmol (nanomoles); gm (grams); mg (milligrams); µg (micrograms); pg (picograms); L (liters); ml and mL (milliliters); µl and µL (microliters); cm (centimeters); mm (millimeters); µm (micrometers); nm (nanometers); U (units); MW (molecular weight); sec (seconds); min(s) (minute/minutes); h(s) and hr(s) (hour/hours); ° C. (degrees Centigrade); QS (quantity sufficient); ND (not done); rpm (revolutions per minute); $H_2O$ (water); $dH_2O$ (deionized water); (HCl (hydrochloric acid); aa (amino acid); by (base pair); kb (kilobase pair); kD (kilodaltons); $MgCl_2$ (magnesium chloride); NaCl (sodium chloride); w/v (weight to volume); v/v (volume to volume); g (gravity); OD (optical density); ppm (parts per million); m- (meta-); o- (ortho-); p- (para-); BCE (BCE103 cellulase); Glu-BL (*Bacillus licheniformis* glutamyl endopeptidase I); GeoT1 (*Geobacillus stearothermophilus* strain T1 lipase); NEFA (non-esterified fatty acids); p-NP (para-nitrophenyl); and SRI (stain removal index).

Example 1

Cloning and Expression of *Geobacillus stearothermophilus* Lipase (GeoT1)

The *Geobacillus stearothermophilus* lipase (GeoT1) gene was previously identified (Leow et al., *Biosci Biotechnol Biochem*, 68:96-103, 2004), with the sequence set forth as GENBANK Accession No. JC8061.

A. Cloning and Expression of GeoT1 in *Streptomyces lividans*

A synthetic gene encoding the GeoT1 polypeptide was generated based on a codon selection method for improved expression in *S. lividans*. The pKB105 plasmid (described in U.S. Publication No. 2006/0154843) was used as the backbone for expression of the synthetic GeoT1 gene, and is the source of the A4 promoter-Ce1A signal sequence. The pKB267 expression vector was constructed by ligation of pKB105, after digestion with the restriction enzymes NheI and BamHI, to a similarly digested GeoT1 synthetic gene, followed by transformation of *E. coli* cells. The correct sequence of GeoT1 gene in pKB267 was confirmed by DNA sequencing.

pKB267 plasmid DNA was used transformed into protoplast of *S. lividans* g3s3 (described in U.S. Publication No. 2006/0154843). Three successful transformants were selected and transferred into seed shake flasks containing 20 ml of TSG medium supplemented with 50 μg/ml of thiostrepton (pre-dissolved in DMSO). Cultures were grown for 2 days at 30° C. with shaking at 200 rpm. Three milliliters of the two-day cultures from seed shake flasks were transferred to 30 ml of *Streptomyces*-modified production medium II (described in U.S. Publication No. 2006/0154843) and incubated for 3 days at 30° C. with shaking at 200 rpm for GeoT1 production. Production culture broth was collected, centrifuged, and the supernatant was used for SDS-PAGE protein analysis and lipase activity assays.

B. Cloning and Expression of BCE-GeoT1 in *Bacillus subtilis*

The *B. subtilis* expression vector p2JMagk103-lnk2-BBI-AV (Collier et al., *Prot. Expr. Purif.*, 68:146-160, 2009) was digested with the restriction enzymes BamHI and HindIII. The DNA fragment lacking the BBI-AV gene sequence was isolated and used as the expression backbone. Ligation of this fragment to a similarly digested synthetic gene encoding the GeoT1 enzyme resulted in the generation of a fusion gene encoding a BCE103 cellulase amino-terminus and a GeoT1 carboxy-terminus (BCE-GeoT1).

In the BCE-GeoT1 fusion protein, the BCE103 cellulase is connected to GeoT1 with a linker that is sensitive to cleavage by acid/heat or by treatment with a glutamyl endopeptidase (e.g., Glu-BL, glutamyl endopeptidase I from *Bacillus licheniformis*) (Vogtentanz, *Prot. Expr. Purif.*, 55:40-52, 2007; and Collier et al., *Prot. Expr. Purif.*, 68:146-160, 2009). Thus although GeoT1 is active as a fusion protein, if desired, GeoT1 can be cleaved from the BCE103 cellulase fusion partner. Briefly, following fusion protein production in shake flasks, efficient cleavage of the fusion protein in the cell-free broth can be accomplished by overnight treatment at 37° C. with 2 μg/ml Glu-BL.

The nucleotide sequence of the *Geobacillus stearothermophilus* lipase (GeoT1) gene used for cloning into the *Streptomyces lividans* expression vector (the NheI and BamHI sites used for cloning are shown in bold) is set forth as SEQ ID NO: 1:

ACTGCGCTAGCCGGCCCCCGGCACAGGCCGCCAGCCTCCGCGCCAACG

ACGCCCCATCGTGCTGCTCCACGGTTTCACGGGCTGGGGCGGGAGGA

GATGTTCGGCTTCAAGTACTGGGCGGCGTGCGCGGGGACATCGAGCAG

TGGCTGAACGACAACGGCTACCGCACGTTCACGCTGGCCGTCGGCCCCC

TCTCCTCCAACTGGGACCGCGCCTGCGAGGCGTACGCGCAGCTGGTCGG

CGGCACGGTCGACTACGGGGCGGCCCACGCGGCCAAGCACGGCCACGCC

CGGTTCGGTCGGACGTACCCGGGCCTGCTGCCGGAGCTGAAGCGCGGTG

GCCGCATCCACATCATCGCGCACAGCCAGGGCGGCCAGACGGCCCGCAT

GCTGGTCAGCCTGCTCGAGAACGGGTCCCAGGAGGAGCGCGAGTACGCC

AAGGCCCACAACGTCAGCCTGTCGCCGCTGTTCGAAGGCGGGCACCACT

TCGTGCTGTCCGTGACGACCATCGCCACCCCGCACGACGGTACCACCCT

CGTGAACATGGTCGACTTCACCGACCGCTTCTTCGACCTCCAGAAGGCG

GTGCTGGAGGCGGCGGCCGTCGCCTCCAACGTGCCGTACACCTCGCAGG

TCTACGACTTCAAGCTGGACCAGTGGGGCCTCCGGCGCCAGCCGGGGGA

GAGCTTCGACCACTACTTCGAGCGCCTGAAGCGGTCCCCGGTGTGGACC

TCCACGGACACCGCGCGCTACGACCTCAGCGTGTCCGGCGCCGAGAAGC

TGAACCAGTGGGTCCAGGCGTCGCCCAACACCTACTACCTCTCGTTCAG

CACCGAGCGGACCTACCGCGGCGCGCTGACCGGGAACCACTACCCCGAG

CTGGGTATGAACGCCTTCAGCGCGGTCGTGTGCGCGCCGTTCCTGGGGT

CGTACCGGAACCCGACGCTGGGCATCGACGACCGCTGGCTGGAGAACGA

CGGCATCGTCAACACGGTCAGCATGAACGGTCCGAAGCGGGGCTCGAGC

GACCGGATCGTCCCCTACGACGGCACCCTGAAGAAGGGCGTCTGGAACG

ACATGGGCACCTACAACGTCGACCACCTGGAGATCATCGGCGTGGACCC

GAACCCGTCCTTCGACATCCGCGCGTTCTACCTGCGGCTGGCGGAACAG

CTGGCGTCCCTGCAGCCCTGACAATGGGGATCCGCGA

The nucleotide sequence of the *Geobacillus stearothermophilus* lipase (GeoT1) synthetic gene used to create the BCE-GeoT1 fusion protein is set forth as SEQ ID NO: 2:

GGATCCAGACGATGAGGCATCTCTTCGCGCTAACGATGCACCTATCGTT

CTTTTACACGGCTTCACCGGTTGGGGACGCGAAGAAATGTTCGGTTTCA

AATACTGGGGAGGCGTTAGAGGCGATATCGAACAATGGTTAAACGATAA

CGGATACCGCACATTCACTCTTGCAGTAGGCCCGTTATCTAGCAACTGG

GATCGTGCTTGTGAAGCATATGCACAACTTGTTGGCGGAACAGTAGATT

ACGGTGCTGCACACGCGGCTAAACACGGACATGCTAGATTCGGTCGCAC

ATACCCGGGATTACTTCCTGAACTGAAAAGAGGCGGACGCATCCACATC

ATTGCACACTCTCAAGGTGGACAAACAGCTAGAATGTTAGTTAGCCTTT

TAGAAAACGGCTCTCAAGAAGAACGTGAATACGCAAAAGCTCACAACGT

AAGCCTTTCACCTTTATTCGAGGGAGGTCACCACTTCGTTTTGAGCGTA
ACAACTATCGCAACACCTCACGATGGCACAACTCTTGTAAACATGGTTG
ATTTCACAGATAGATTCTTCGATTTACAAAAAGCTGTACTTGAAGCTGC
GGCAGTTGCTAGCAACGTACCTTACACATCTCAAGTTTACGATTTCAAA
TTAGATCAATGGGGCCTTCGCAGACAACCAGGAGAATCATTTGATCACT
ACTTCGAGCGTTTAAAAAGAAGCCCTGTTTGGACTTCTACTGATACAGC
ACGCTACGACTTAAGCGTTAGCGGCGCTGAAAAACTTAACCAATGGGTA
CAAGCATCTCCTAACACATACTACCTTAGCTTCTCAACAGAAAGAACTT
ACCGCGGAGCTTTAACAGGCAACCACTACCCAGAACTTGGCATGAACGC
GTTCAGCGCTGTTGTATGCGCACCTTTCCTAGGTTCTTACCGCAACCCA
ACATTAGGTATCGATGATAGATGGCTTGAAAACGATGGTATCGTTAACA
CAGTAAGCATGAACGGACCTAAACGCGGGAGCTCTGATAGAATCGTTCC
TTATGATGGTACACTTAAGAAAGGAGTATGGAACGATATGGGTACATAC
AACGTTGATCATTTAGAAATTATCGGAGTAGATCCAAACCCTTCTTTTG
ATATTAGAGCTTTCTACCTTCGTTTAGCAGAACAACTTGCTTCTCTGCA
GCCTTAAAAGCTT

The nucleotide sequence of the gene encoding the BCE-GeoT1 fusion protein is set forth as SEQ ID NO: 3:

GATGATTATTCAGTTGTAGAGGAACATGGGCAACTAAGTATTAGTAACG
GTGAATTAGTCAATGAACGAGGCGAACAAGTTCAGTTAAAAGGGATGAG
TTCCCATGGTTTGCAATGGTACGGTCAATTTGTAAACTATGAAAGCATG
AAATGGCTAAGAGATGATTGGGGAATAACTGTATTCCGAGCAGCAATGT
ATACCTCTTCAGGAGGATATATTGACGATCCATCAGTAAAGGAAAAAGT
AAAAGAGACTGTTGAGGCTGCGATAGACCTTGGCATATATGTGATCATT
GATTGGCATATCCTTTCAGACAATGACCCGAATATATATAAAGAAGAAG
CGAAGGATTTCTTTGATGAAATGTCAGAGTTGTATGGAGACTATCCGAA
TGTGATATACGAAATTGCAAATGAACCGAATGGTAGTGATGTTACGTGG
GACAATCAAATAAAACCGTATGCAGAAGAAGTGATTCCGGTTATTCGTG
ACAATGACCCTAATAACATTGTTATTGTAGGTACAGGTACATGGAGTCA
GGATGTCCATCATGCAGCCGATAATCAGCTTGCAGATCCTAACGTCATG
TATGCATTTCATTTTTATGCAGGAACACATGGACAAAATTTACGAGACC
AAGTAGATTATGCATTAGATCAAGGAGCAGCGATATTTGTTAGTGAATG
GGGGACAAGTGCAGCTACAGGTGATGGTGGTGTGTTTTTAGATGAAGCA
CAAGTGTGGATTGACTTTATGGATGAAAGAAATTTAAGCTGGGCCAACT
GGTCTCTAACGCATAAGGATGAGTCATCTGCAGCGTTAATGCCAGGTGC
AAATCCAACTGGTGGTTGGACAGAGGCTGAACTATCTCCATCTGGTACA
TTTGTGAGGGAAAAAATAAGAGAATCAGCATCTGACAACAATGATCCCA
TACCGGATCCAGACGATGAGGCATCTCTTCGCGCTAACGATGCACCTAT
CGTTCTTTTACACGGCTTCACCGGTTGGGACGCGAAGAAATGTTCGGT
TTCAAATACTGGGGAGGCGTTAGAGGCGATATCGAACAATGGTTAAACG

ATAACGGATACCGCACATTCACTCTTGCAGTAGGCCCGTTATCTAGCAA
CTGGGATCGTGCTTGTGAAGCATATGCACAACTTGTTGGCGGAACAGTA
GATTACGGTGCTGCACACGCGGCTAAACACGGACATGCTAGATTCGGTC
GCACATACCCGGGATTACTTCCTGAACTGAAAAGAGGCGGACGCATCCA
CATCATTGCACACTCTCAAGGTGGACAAACAGCTAGAATGTTAGTTAGC
CTTTTAGAAAACGGCTCTCAAGAAGAACGTGAATACGCAAAAGCTCACA
ACGTAAGCCTTTCACCTTTATTCGAGGGAGGTCACCACTTCGTTTTGAG
CGTAACAACTATCGCAACACCTCACGATGGCACAACTCTTGTAAACATG
GTTGATTTCACAGATAGATTCTTCGATTTACAAAAAGCTGTACTTGAAG
CTGCGGCAGTTGCTAGCAACGTACCTTACACATCTCAAGTTTACGATTT
CAAATTAGATCAATGGGGCCTTCGCAGACAACCAGGAGAATCATTTGAT
CACTACTTCGAGCGTTTAAAAAGAAGCCCTGTTTGGACTTCTACTGATA
CAGCACGCTACGACTTAAGCGTTAGCGGCGCTGAAAAACTTAACCAATG
GGTACAAGCATCTCCTAACACATACTACCTTAGCTTCTCAACAGAAAGA
ACTTACCGCGGAGCTTTAACAGGCAACCACTACCCAGAACTTGGCATGA
ACGCGTTCAGCGCTGTTGTATGCGCACCTTTCCTAGGTTCTTACCGCAA
CCCAACATTAGGTATCGATGATAGATGGCTTGAAAACGATGGTATCGTT
AACACAGTAAGCATGAACGGACCTAAACGCGGGAGCTCTGATAGAATCG
TTCCTTATGATGGTACACTTAAGAAAGGAGTATGGAACGATATGGGTAC
ATACAACGTTGATCATTTAGAAATTATCGGAGTAGATCCAAACCCTTCT
TTTGATATTAGAGCTTTCTACCTTCGTTTAGCAGAACAACTTGCTTCTC
TGCAGCCTTAA

The amino acid sequence of the mature GeoT1 enzyme is set forth as SEQ ID NO: 4:

ASLRANDAPIVLLHGFTGWGREEMFGFKYWGGVRGDIEQWLNDNGYRTF
TLAVGPLSSNWDRACEAYAQLVGGTVDYGAAHAAKHGHARFGRTYPGLL
PELKRGGRIHIIAHSQGGQTARMLVSLLENGSQEEREYAKAHNVSLSPL
FEGGHHFVLSVTTIATPHDGTTLVNMVDFTDRFFDLQKAVLEAAAVASN
VPYTSQVYDFKLDQWGLRRQPGESFDHYFERLKRSPVWTSTDTARYDLS
VSGAEKLNQWVQASPNTYYLSFSTERTYRGALTGNHYPELGMNAFSAVV
CAPFLGSYRNPTLGIDDRWLENDGIVNTVSMNGPKRGSSDRIVPYDGTL
KKGVWNDMGTYNVDHLEIIGVDPNPSFDIRAFYLRLAEQLASLQP

The amino acid sequence of the BCE-GeoT1 fusion protein is set forth as SEQ ID NO: 5:

DDYSVVEEHGQLSISNGELVNERGEQVQLKGMSSHGLQWYGQFVNYESM
KWLRDDWGITVFRAAMYTSSGGYIDDPSVKEKVKETVEAAIDLGIYVII
DWHILSDNDPNIYKEEAKDFFDEMSELYGDYPNVIYEIANEPNGSDVTW
DNQIKPYAEEVIPVIRDNDPNNIVIVGTGTWSQDVHHAADNQLADPNVM
YAFHFYAGTHGQNLRDQVDYALDQGAAIFVSEWGTSAATGDGGVFLDEA
QVWIDFMDERNLSWANWSLTHKDESSAALMPGANPTGGWTEAELSPSGT

-continued

FVREKIRESASDNNDPIPDPDDDEASLRANDAPIVLLHGFTGWGREEMFG

FKYWGGVRGDIEQWLNDNGYRTFTLAVGPLSSNWDRACEAYAQLVGGTV

DYGAAHAAKHGHARFGRTYPGLLPELKRGGRIHIIAHSQGGQTARMLVS

LLENGSQEEREYAKAHNVSLSPLFEGGHHFVLSVTTIATPHDGTTLVNM

VDFTDRFFDLQKAVLEAAAVASNVPYTSQVYDFKLDQWGLRRQPGESFD

HYFERLKRSPVWTSTDTARYDLSVSGAEKLNQWVQASPNTYYLSFSTER

TYRGALTGNHYPELGMNAFSAVVCAPFLGSYRNPTLGIDDRWLENDGIV

NTVSMNGPKRGSSDRIVPYDGTLKKGVWNDMGTYNVDHLEIIGVDPNPS

FDIRAFYLRLAEQLASLQP

The BCE-GeoT1 fusion protein was produced in *Bacillus subtilis* cells (degU$^{Hy}$32, oppA, ΔspoIIE, ΔaprE, ΔnprE, Δepr, ΔispA, Δbpr, Δvpr, ΔwprA, Δmpr-ybfJ, ΔnprB, amyE::xylRPxylAcomK-ermC) using previously described methods (Vogtentanz, *Prot. Expr. Purif*, 55:40-52, 2007).

Example 2

Isolation of GeoT1 and Purification of BCE-GeoT1 Protein Isolation of GeoT1 Protein For production of recombinant GeoT1, the *S. lividans* expression strain was cultured in shake flasks. The culture was harvested after 96 hr of growth at 28° C. A clarified broth was prepared by centrifugation, and used for characterization of GeoT1.

For purification of BCE-GeoT1, ultra-filtered concentrate derived from a 14-L-scale batch fermentation was diluted 5-fold with 50 mM Tris-HCl, pH 8.0, buffer, and ammonium sulfate was added to a final concentration of 1 M. The sample was filtered with a 0.8 micron glass fiber filter. Flow-through was collected and used for further purification on a FastFlow Phenyl Sepharose column equilibrated with 1 M ammonium sulfate in 50 mM Tris-HCl, pH 8.0, buffer. Sample was loaded at half the equilibration flow rate (12 ml/min) and washed with equilibration buffer after loading. A gradient was used to reduce the concentration from 1 M ammonium sulfate to 0 M in buffer. Contaminant proteins were washed off the column with the 50 mM Tris, pH 8.0, buffer. The BCE-GeoT1 protein was eluted with a buffer containing 50 mM Tris HCl, pH 8.0, and 40% propylene glycol. Fractions were assayed using the para-nitrophenyl (pNP) butyrate assay described below. Pooled fraction were loaded onto a Q-sepharose (20 mm×200 mm) column, with 25 mM Tris, pH 8.0, buffer, and fractions collected while running a 0 to 400 mM NaCl gradient. Fractions are assayed using the pNP butyrate substrate, and those with lipase activity are pooled and concentrated using a stir cell with a 10K membrane.

The method described above is also suitable for purification of the GeoT1 protein lacking a fusion partner.

Example 3

Hydrolysis of p-Nitrophenyl Esters by GeoT1 and BCE-GeoT1

The GeoT1 protein and BCE-GeoT1 fusion protein were assayed for lipase activity on three different para-nitrophenyl (pNP) ester substrates with varying ester chain lengths to determine the chain length preference of GeoT1. Table 3-1 provides details of the pNP ester substrates.

TABLE 3-1

| pNP Ester Substrates | | | |
|---|---|---|---|
| Substrate | Abbr | Chain-length | Source |
| p-nitrophenyl butyrate | pNB | C4:0 | Sigma (CAS 2635-84-9) |
| p-nitrophenyl caprylate | pNO | C8:0 | Sigma (CAS 1956-10-1) |
| p-nitrophenyl palmitate | pNP | C16:0 | Sigma (CAS 1492-30-4) |

A reaction emulsion with pNP ester substrate was prepared using 0.8 mM pNP ester suspended in ethanol (5%) in one of 2 buffers: 0.05 M HEPES, 6 mM CaCl$_2$ adjusted to pH 8.2, or 0.05 M CAPS, 6 mM CaCl$_2$ adjusted to pH 10. To aid in the emulsification of the pNP-esters, 0.5% gum Arabic was added to both buffers.

The pNP-ester/buffer suspensions were mixed, ultra-sonicated for 2 minutes and 100 μL of each was transferred to 96-well microtiter plate wells containing 20 μL enzyme samples. The generation of liberated pNP was monitored over a period of 15 minutes at OD$_{405}$ nm and corrected using blank values (no enzyme). The pNP product generated per minute was recorded and normalized to the added enzyme sample in the well (delta OD/min per added mg enzyme). The relative enzyme activity on the different substrates was calculated, and the rate of product release obtained using each substrate was normalized to the highest activity (e.g., activity on the pNP-caprylate substrate was set to 100).

TABLE 3-2

| Chain Length Preference of Geo T1 and BCE-GeoT1 | | | | | |
|---|---|---|---|---|---|
| | pH 8.2 | | | pH 10 | |
| | Butyrate | Caprylate | Palmitate | Caprylate | Palmitate |
| GeoT1 | 40 | 100 | 30 | 100 | 10 |
| BCE GeoT1 | 20 | 100 | 30 | 100 | 30 |

As shown in Table 3-2, Geo T1 and BCE-GeoT1 proteins show activity towards pNP-ester substrates from 4 to 16 carbons long, at both pH 8 and 10.

Example 4

Triglyceride Hydrolysis by BCE-GeoT1 in the Presence and Absence of Detergent

BCE-GeoT1 was assayed for hydrolysis of trioctanoate and trioleate substrates in the presence and absence of a detergent. The glyceryl trioctanoate (CAS 538-23-8) and glyceryl trioleate (CAS 122-32-7) substrates were purchased from Sigma™. The following commercially available detergents were used for this experiment: (1) OMO color, liquid detergent, from Unilever; (2) Ariel™ color, liquid detergent, from Procter & Gamble; (3) Biotex™ color, powder detergent, from Blumøller™; and (4) Ariel™ color, powder detergent, from Procter & Gamble.

OMO Color Liquid Detergent

The OMO color liquid detergent composition comprises 5-15% anionic surfactants and nonionic surfactants, <5% soap, cationic surfactants, phosphonates, perfume, butylphenyl methylptopionate, citronellol, enzymes, and benzisothiazolinone. The OMO color liquid detergent contains the following surfactants: C12-15 pareth-7, sodium dodecylbenzene sulfonate, sodium laureth sulfate, and sodium hydrogenated cocoate.

Ingredients of the OMO color liquid detergent are as follows: water, C12-15 pareth-7, sodium dodecylbenzene sulfonate, sodium laureth sulfate, propylene glycol, sodium hydrogenated cocoate, sodium diethylenetriamine pentamethylene phosphonate, perfume, sodium sulfate, sodium hydroxide, butylphenyl methylpropional, sorbitol, citronellol, protease, benzisothiazolinone, boronic acid, (4-formylphenyl), amylase, CI-45100, and CI-42051.

Ariel™ Color Liquid Detergent

The Ariel™ color liquid detergent composition comprises 5-15% anionic surfactants, <5% nonionic surfactants, phosphonates, soap, enzymes, perfume, butylphenyl methylptopionate, and geraniol. The Ariel™ color liquid detergent contains the following surfactants: sodium dodecylbenzene sulfonate, C12-14 pareth-7, sodium laureth sulfate, and C12-14 pareth-4.

Ingredients of the Ariel™ color liquid detergent are as follows: sodium dodecylbenzene sulfonate, sodium citrate, sodium palm kernelate, C12-14 pareth-7, sodium laureth sulfate, alcohol denatured, C14-15 pareth-4, mea-borate, sulfated ethoxylated hexamethylenediamine quaternized, propylene glycol, water, hydrogenated castor oil, parfum, protease, sodium diethylenetriamine pentamethylene phosphonate, C12-15 alcohols, glycosidase, polyvinylpyridine-n-oxide, polyethylene glycol, sodium sulfate, sodium chloride, dimethicone, colorant, silica, butylphenyl methylpropional, and geraniol.

Biotex™ Color Powder Detergent

The Biotex™ color powder detergent composition comprises 15-30% zeolite, 5-15% anionic surfactants, <5% soap, polycarboxylates, phosphonates, enzymes, and perfume. The Biotex™ color powder detergent contains the C12-15 pareth-7 surfactant.

Ingredients of the Biotex™ color liquid detergent are as follows: zeolite, sodium carbonate, sodium sulfate, water, C12-15 pareth-7, sodium tallowate, maleic acid-acrylic acid copolymer sodium salt, sodium citrate, laureth-7, cellulose gum, laureth-5, sodium EDTMP, parfum, tetrasodium etidronate, subtilisin, amylase, triacylglycerol lipase, and cellulase.

Ariel™ Color Powder Detergent

The Ariel™ color powder detergent composition comprises 5-15% anionic surfactants, zeolite, <5% nonionic surfactants, polycarboxylates, phosphonates, enzymes, perfume, hexyl cinnamal, limonene, and butylphenyl methylptopionate. The Ariel™ color powder detergent contains the following surfactants: sodium dodecylbenzene sulfonate, sodium C12-15 pareth sulfate, and C12-15 pareth-7.

Ingredients of the Ariel™ color powder detergent are as follows: sodium sulfate, sodium carbonate, bentonite, sodium dodecylbenzene sulfonate, sodium silicoaluminate, sodium C12-15 pareth sulfate, sodium acrylic acid/MA copolymer, water, citric acid, dimethicone, C12-15 pareth-7, magnesium sulfate, sodium dodecylbenzene sulfonate, parfum, cellulose gum, sodium chloride, tetrasodium etidronate, sodium toluenesulfonate, starch, sodium octenyl succinate, polyethylene glycol, glycosidase, trisodium ethylenediamine disuccinate, sulfuric acid, sodium glycollate, phenylpropyl ether methicone, sodium polyacrylate, dodecylbenzene sulfonic acid, dichlorodimethylsilane RX with silica, colorant, glycerine, sodium laureth sulfate, sodium hydroxide, C10-16 alkylbenzene sulfonic acid, butylphenyl methylpropional, hexyl cinnamal, and linalool.

The detergents were heat-inactivated as follows: the liquid detergents were placed in a water bath at 95° C. for 2 hours, while 0.1 g/mL preparations in water of the powder detergents were boiled on a hot plate for 1 hour. Heat treatments inactivate the enzymatic activity of any protein components in commercial detergent formulas, while retaining the properties of the non-enzymatic detergent components. Following heating, the detergents are diluted and assayed for lipase enzyme activity.

Reaction emulsions of trioctanoate and trioleate were prepared from 0.4% trioctanoate or trioleate pre-suspended in ethanol (5%), in one of 2 buffers: 0.05 M HEPES adjusted to pH 8.2, or 0.05 M CAPS adjusted to pH 10. For both buffers water hardness was adjusted to 6 mM $CaCl_2$. Two percent gum Arabic was added to both buffers to aid in the emulsification of the triglyceride.

Reaction emulsions of trioctanoate in each of the detergents was prepared from 0.4% trioctanoate pre-suspended in ethanol (5%), in one of 2 buffers: 0.05 M HEPES, adjusted to pH 8.2, or 0.05 M CAPS adjusted to pH 10. For both buffers water hardness was adjusted to 24 FH. The final assay mixtures contained varying amounts of detergents, to aid in the emulsification of the triglyceride.

The reaction emulsions were made by applying high shear mixing for 2 minutes (24000 $m^{-1}$, Ultra Turrax T25, Janke & Kunkel), and then transferring 150 µL to 96-well microtiter plate wells already containing 30 µL enzyme samples. Free fatty acid generation was measured using an in vitro enzymatic colorimetric assay for the quantitative determination of non-esterified fatty acids (NEFA). This method is specific for free fatty acids, and relies upon the acylation of coenzyme A (CoA) by the fatty acids in the presence of added acyl-CoA synthetase. The acyl-CoA thus produced is oxidized by added acyl-CoA oxidase with generation of hydrogen peroxide, in the presence of peroxidase. This permits the oxidative condensation of 3-methyl-N-ethyl-N(β-hydroxyethyl)-aniline with 4-aminoantipyrine to form a purple colored adduct which can be measured colorimetrically. The amount of free fatty acids generated after a 6 minute incubation at 30° C. was determined using the materials in a NEFA HR(2) kit (Wako Chemicals GmbH, Germany) by transferring 30 µL of the hydrolysis solution to 96-well microtiter plate wells already containing 120 µL NEFA A solution. Incubation for 3 min at 30° C. was followed by addition of 60 µL NEFA B solution. After incubation for 4.5 min at 30° C. OD at 520 nm was measured.

Table 4-1 shows hydrolysis of trioleate and trioctanoate by BCE-GeoT1. Data for triglyceride hydrolysis was determined as µmol free fatty acid. The results are reported relative to the activity on tri-octanoate (C8) in buffer, which was set to 100.

TABLE 4-1

Trioleate and Trioctanoate Hydrolysis by BCE-GeoT1 in Buffer

| | pH 8.2 | | pH 10 | |
|---|---|---|---|---|
| | Trioctanoate | Trioleate | Trioctanoate | Trioleate |
| BCE GeoT1 | 100 | 20 | 100 | 20 |

Table 4-2 shows trioctanoate hydrolysis by BCE-GeoT1 in the presence or absence of various detergents at pH 8.2 and pH 10.0. Data for trioctanoate hydrolysis in the presence of detergent is reported as percent trioctanoate hydrolysis in the presence of detergent relative to trioctanoate hydrolysis in the absence of detergent at both pH values tested.

TABLE 4-2

Trioctanoate Hydrolysis by BCE-GeoT1 in Detergent Compositions

| pH | No detergent | 1 ml OMO liquid/L | 2.6 ml OMO liquid/L | 1 ml Ariel™ liquid/L | 2.5 mL Ariel™ liquid/L |
|---|---|---|---|---|---|
| 8.2 | 100 | 50 | 10 | 15 | 10 |

| pH | No detergent | 1 g Ariel™ powder/L | 1.7 g Ariel™ powder/L | 1 g BioTex™ powder/L | 2.2 g Biotex™ powder/L |
|---|---|---|---|---|---|
| 10 | 100 | 1 | 1 | 20 | 3 |

BCE-GeoT1 shows lipase activity in various liquid and powder detergents as a function of detergent concentration.

Example 5

Cleaning Performance of BCE-GeoT1

Cleaning performance of BCE-GeoT1 on stained fabrics was tested in a microswatch assay format. Stain removal experiments were carried out using a lipid-containing technical stain (CS-61 swatches, purchased from Center for Testmaterials, Netherlands) set in a 24-well plate format (Nunc, Denmark). Each assay well was set to contain a pre-cut 13 mm piece of CS-61 swatch. Swatches were pre-read using a reflectometer (CR-400, Konica Minolta) before placement in the 24-well plate.

The buffers used were 20 mM HEPES (final concentration), pH 8.2, for testing liquid detergents, and 20 mM CAPS (final concentration), pH 10.0, for testing powder detergents. Water hardness was adjusted to 24FH for both buffers. The commercially available, heat-inactivated detergents used were the same as described in the triglyceride hydrolysis assay of Example 4.

Briefly, 900 µl of the appropriate buffer was added to each swatch-containing well of the 24-well plate. To initiate the reaction, enzyme samples were added at a volume of 100 µL into each well. The plates were shaken for 30 minutes at 200 rpm at 37° C. After incubation, the reaction buffer was removed and the fabric in each well was rinsed with 1 mL distilled water three times. After removing the rinsed swatches, the swatches were dried at 50° C. for 4 hours before reflectance was measured. Cleaning was calculated as the difference of the post- and pre-cleaning reflectometry measurements for each swatch. Measurement of reflectance was performed by taking CIE L*a*b* measurements with a spectrophotometer (CR-400, Konica Minolta). A difference in stain removal index ($\Delta$SRI) values of the washed fabric were calculated in relation to the unwashed fabrics using the formula:

$$\text{Total color difference } (\Delta SRI) = \sqrt{(\Delta L^2 + \Delta a^2 + \Delta b^2)}$$

In this equation, $\Delta L$, $\Delta a$, $\Delta b$, are differences in CIE L*, CIE a*, and CIE b* values respectively before and after cleaning, where L* defines lightness and a* and b* define chromaticity (see, e.g., Precise Color Communication: Color Control From Perception to Instrumentation, Konica Minolta Sensing, Inc., Osaka, Japan, pp. 32-59, 1998).

TABLE 5-1

Cleaning Performance of BCE-GeoT1 on Stained Fabric

| | 0.4 g/L detergent | | | |
|---|---|---|---|---|
| | Powder detergent | | Liquid detergent | |
| | Ariel™ | Biotex™ | Ariel™ | OMO |
| BCE-GeoT1 | +++ | +++ | +++ | +++ |

BCE-GeoT1 exhibited significant cleaning performance in OMO color liquid detergent from Unilever; Ariel™ color liquid detergent from Procter & Gamble, Ariel™ color powder detergent from Procter & Gamble, and Biotex™ color powder detergent from Blumøller™.

Example 6

Liquid Laundry Detergent Compositions Comprising GeoT1

In this example, various formulations for liquid laundry detergent compositions are provided. In each of these formulations, GeoT1 or BCE-GeoT1 is included at a concentration of from about 0.0001 to about 10 weight-percent. In some alternative embodiments, other concentrations will find use, as determined by the formulator, based on their needs.

TABLE 6-1

Liquid Laundry Detergent Compositions

| | Formulations | | | | |
|---|---|---|---|---|---|
| Compound | I | II | III | IV | V |
| LAS | 24.0 | 32.0 | 6.0 | 3.0 | 6.0 |
| NaC$_{16}$-C$_{17}$ HSAS | — | — | — | 5.0 | — |
| C$_{12}$-C$_{15}$ AE$_{1.8}$S | — | — | 8.0 | 7.0 | 5.0 |
| C$_8$-C$_{10}$ propyl dimethyl amine | 2.0 | 2.0 | 2.0 | 2.0 | 1.0 |
| C$_{12}$-C$_{14}$ alkyl dimethyl amine oxide | — | — | — | — | 2.0 |
| C$_{12}$-C$_{15}$ AS | — | — | 17.0 | — | 8.0 |
| CFAA | — | 5.0 | 4.0 | 4.0 | 3.0 |
| C$_{12}$-C$_{14}$ Fatty alcohol ethoxylate | 12.0 | 6.0 | 1.0 | 1.0 | 1.0 |
| C$_{12}$-C$_{18}$ Fatty acid | 3.0 | — | 4.0 | 2.0 | 3.0 |
| Citric acid (anhydrous) | 4.5 | 5.0 | 3.0 | 2.0 | 1.0 |
| DETPMP | — | — | 1.0 | 1.0 | 0.5 |
| Monoethanolamine | 5.0 | 5.0 | 5.0 | 5.0 | 2.0 |
| Sodium hydroxide | — | — | 2.5 | 1.0 | 1.5 |
| 1N HCl aqueous solution | #1 | #1 | — | — | — |
| Propanediol | 12.7 | 14.5 | 13.1 | 10. | 8.0 |
| Ethanol | 1.8 | 2.4 | 4.7 | 5.4 | 1.0 |
| DTPA | 0.5 | 0.4 | 0.3 | 0.4 | 0.5 |
| Pectin Lyase | — | — | — | 0.005 | — |
| Amylase | 0.001 | 0.002 | — | — | — |
| Cellulase | — | — | 0.0002 | — | 0.0001 |
| Lipase | 0.1 | — | 0.1 | — | 0.1 |
| NprE (optional) | 0.05 | 0.3 | — | 0.5 | 0.2 |
| PMN | — | — | 0.08 | — | — |
| Protease A (optional) | — | — | — | — | 0.1 |
| Aldose Oxidase | — | — | 0.3 | — | 0.003 |
| ZnCl2 | 0.1 | 0.05 | 0.05 | 0.05 | 0.02 |
| Ca formate | 0.05 | 0.07 | 0.05 | 0.06 | 0.07 |
| DETBCHD | — | — | 0.02 | 0.01 | — |
| SRP1 | 0.5 | 0.5 | — | 0.3 | 0.3 |
| Boric acid | — | — | — | — | 2.4 |
| Sodium xylene sulfonate | — | — | 3.0 | — | — |
| Sodium cumene sulfonate | — | — | — | 0.3 | 0.5 |
| DC 3225C | 1.0 | 1.0 | 1.0 | 1.0 | 1.0 |
| 2-butyl-octanol | 0.03 | 0.04 | 0.04 | 0.03 | 0.03 |

TABLE 6-1-continued

Liquid Laundry Detergent Compositions

| Compound | I | II | III | IV | V |
|---|---|---|---|---|---|
| Brightener 1 | 0.12 | 0.10 | 0.18 | 0.08 | 0.10 |
| Balance to 100% perfume/dye and/or water | | | | | |

1: Add 1N HCl aq. soln to adjust the neat pH of the formula in the range from about 3 to about 5. The pH of Examples above 6(I)-(II) is about 5 to about 7, and of 6(III)-(V) is about 7.5 to about 8.5.

Example 7

Liquid Hand Dishwashing Detergent Compositions Comprising GeoT1

In this example, various hand dish liquid detergent formulations are provided. In each of these formulations, GeoT1 or BCE-GeoT1 is included at a concentration of from about 0.0001 to about 10 weight-percent. In some alternative embodiments, other concentrations will find use, as determined by the formulator, based on their needs.

TABLE 7-1

Liquid Hand Dishwashing Detergent Compositions

| Compound | I | II | III | IV | V | VI |
|---|---|---|---|---|---|---|
| $C_{12}$-$C_{15}$ $AE_{1.8}S$ | 30.0 | 28.0 | 25.0 | — | 15.0 | 10.0 |
| LAS | — | — | — | 5.0 | 15.0 | 12.0 |
| Paraffin Sulfonate | — | — | — | 20.0 | — | — |
| $C_{10}$-$C_{18}$ Alkyl Dimethyl Amine Oxide | 5.0 | 3.0 | 7.0 | — | — | — |
| Betaine | 3.0 | — | 1.0 | 3.0 | 1.0 | — |
| $C_{12}$ poly-OH fatty acid amide | — | — | — | 3.0 | — | 1.0 |
| $C_{14}$ poly-OH fatty acid amide | — | 1.5 | — | — | — | — |
| $C_{11}E_9$ | 2.0 | — | 4.0 | — | — | 20.0 |
| DTPA | — | — | — | — | 0.2 | — |
| Tri-sodium Citrate dehydrate | 0.25 | — | — | 0.7 | — | — |
| Diamine | 1.0 | 5.0 | 7.0 | 1.0 | 5.0 | 7.0 |
| $MgCl_2$ | 0.25 | — | — | 1.0 | — | — |
| nprE (optional) | 0.02 | 0.01 | — | 0.01 | — | 0.05 |
| PMN | — | — | 0.03 | — | 0.02 | — |
| Protease A (optional) | — | 0.01 | — | — | — | — |
| Amylase | 0.001 | — | — | 0.002 | — | 0.001 |
| Aldose Oxidase | 0.03 | — | 0.02 | — | 0.05 | — |
| Sodium Cumene Sulphonate | — | — | — | 2.0 | 1.5 | 3.0 |
| PAAC | 0.01 | 0.01 | 0.02 | — | — | — |
| DETBCHD | — | — | — | 0.01 | 0.02 | 0.01 |
| Balance to 100% perfume/dye and/or water | | | | | | |

The pH of Examples 7(I)-(VI) is about 8 to about 11

Example 8

Liquid Automatic Dishwashing Detergent Compositions Comprising GeoT1

In this example, various liquid automatic dishwashing detergent formulations are provided. In each of these formulations, GeoT1 or BCE-GeoT1 is included at a concentration of from about 0.0001 to about 10 weight-percent. In some alternative embodiments, other concentrations will find use, as determined by the formulator, based on their needs.

TABLE 8-1

Liquid Automatic Dishwashing Detergent Compositions

| Compound | I | II | III | IV | V |
|---|---|---|---|---|---|
| STPP | 16 | 16 | 18 | 16 | 16 |
| Potassium Sulfate | — | 10 | 8 | — | 10 |
| 1,2 propanediol | 6.0 | 0.5 | 2.0 | 6.0 | 0.5 |
| Boric Acid | — | — | — | 4.0 | 3.0 |
| $CaCl_2$ dihydrate | 0.04 | 0.04 | 0.04 | 0.04 | 0.04 |
| Nonionic | 0.5 | 0.5 | 0.5 | 0.5 | 0.5 |
| nprE (optional) | 0.1 | 0.03 | — | 0.03 | — |
| PMN | — | — | 0.05 | — | 0.06 |
| Protease B (optional) | — | — | — | 0.01 | — |
| Amylase | 0.02 | — | 0.02 | 0.02 | — |
| Aldose Oxidase | — | 0.15 | 0.02 | — | 0.01 |
| Galactose Oxidase | — | — | 0.01 | — | 0.01 |
| PAAC | 0.01 | — | — | 0.01 | — |
| DETBCHD | — | 0.01 | — | — | 0.01 |
| Balance to 100% perfume/dye and/or water | | | | | |

Example 9

Granular and/or Tablet Laundry Compositions Comprising GeoT1

This example provides various formulations for granular and/or tablet laundry detergents. In each of these formulations, GeoT1 or BCE-GeoT1 is included at a concentration of from about 0.0001 to about 10 weight percent. In some alternative embodiments, other concentrations will find use, as determined by the formulator, based on their needs.

TABLE 9-1

Granular and/or Tablet Laundry Compositions

| Compound | I | II | III | IV | V |
|---|---|---|---|---|---|
| Base Product | | | | | |
| $C_{14}$-$C_{15}$AS or TAS | 8.0 | 5.0 | 3.0 | 3.0 | 3.0 |
| LAS | 8.0 | — | 8.0 | — | 7.0 |
| $C_{12}$-$C_{15}AE_3S$ | 0.5 | 2.0 | 1.0 | — | — |
| $C_{12}$-$C_{15}E_5$ or $E_3$ | 2.0 | — | 5.0 | 2.0 | 2.0 |
| QAS | — | — | — | 1.0 | 1.0 |
| Zeolite A | 20.0 | 18.0 | 11.0 | — | 10.0 |
| SKS-6 (dry add) | — | — | 9.0 | — | — |
| MA/AA | 2.0 | 2.0 | 2.0 | — | — |
| AA | — | — | — | — | 4.0 |
| 3Na Citrate $2H_2O$ | — | 2.0 | — | — | — |
| Citric Acid (Anhydrous) | 2.0 | — | 1.5 | 2.0 | — |
| DTPA | 0.2 | 0.2 | — | — | — |
| EDDS | — | — | 0.5 | 0.1 | — |
| HEDP | — | — | 0.2 | 0.1 | — |
| PB1 | 3.0 | 4.8 | — | — | 4.0 |
| Percarbonate | — | — | 3.8 | 5.2 | — |
| NOBS | 1.9 | — | — | — | — |
| NACA OBS | — | — | 2.0 | — | — |
| TAED | 0.5 | 2.0 | 2.0 | 5.0 | 1.00 |
| BB1 | 0.06 | — | 0.34 | — | 0.14 |
| BB2 | — | 0.14 | — | 0.20 | — |
| Anhydrous Na Carbonate | 15.0 | 18.0 | — | 15.0 | 15.0 |
| Sulfate | 5.0 | 12.0 | 5.0 | 17.0 | 3.0 |
| Silicate | — | 1.0 | — | — | 8.0 |
| nprE (optional) | 0.03 | — | 0.1 | 0.06 | — |
| PMN | — | 0.05 | — | — | 0.1 |
| Protease B (optional) | — | 0.01 | — | — | — |
| Protease C (optional) | — | — | — | 0.01 | — |
| Lipase | — | 0.008 | — | — | — |
| Amylase | 0.001 | — | — | — | 0.001 |
| Cellulase | — | 0.0014 | — | — | — |

TABLE 9-1-continued

Granular and/or Tablet Laundry Compositions

| Compound | Formulations | | | | |
|---|---|---|---|---|---|
| | I | II | III | IV | V |
| Pectin Lyase | 0.001 | 0.001 | 0.001 | 0.001 | 0.001 |
| Aldose Oxidase | 0.03 | — | 0.05 | — | — |
| PAAC | — | 0.01 | — | — | 0.05 |
| Balance to 100% Moisture and/or Minors* | | | | | |

*Perfume, dye, brightener/SRP1/Na carboxymethylcellulose/photobleach/MgSO$_4$/PVPVI/suds suppressor/high molecular PEG/clay.

Example 10

Additional Liquid Laundry Detergents Comprising GeoT1

This example provides further formulations for liquid laundry detergents. In each of these formulations, GeoT1 or BCE-GeoT1 is included at a concentration of from about 0.0001 to about 10 weight percent. In some alternative embodiments, other concentrations will find use, as determined by the formulator, based on their needs.

TABLE 10-1

Liquid Laundry Detergents

| Compound | Formulations | | | | | |
|---|---|---|---|---|---|---|
| | I | I | II | III | IV | V |
| LAS | 11.5 | 11.5 | 9.0 | — | 4.0 | — |
| $C_{12}$-$C_{15}AE_{2.85}S$ | — | — | 3.0 | 18.0 | — | 16.0 |
| $C_{14}$-$C_{15}E_{2.5}S$ | 11.5 | 11.5 | 3.0 | — | 16.0 | — |
| $C_{12}$-$C_{13}E_9$ | — | — | 3.0 | 2.0 | 2.0 | 1.0 |
| $C_{12}$-$C_{13}E_7$ | 3.2 | 3.2 | — | — | — | — |
| CFAA | — | — | — | 5.0 | — | 3.0 |
| TPKFA | 2.0 | 2.0 | — | 2.0 | 0.5 | 2.0 |
| Citric Acid (Anhyd.) | 3.2 | 3.2 | 0.5 | 1.2 | 2.0 | 1.2 |
| Ca formate | 0.1 | 0.1 | 0.06 | 0.1 | — | — |
| Na formate | 0.5 | 0.5 | 0.06 | 0.1 | 0.05 | 0.05 |
| ZnCl2 | 0.1 | 0.05 | 0.06 | 0.03 | 0.05 | 0.05 |
| Na Culmene Sulfonate | 4.0 | 4.0 | 1.0 | 3.0 | 1.2 | — |
| Borate | 0.6 | 0.6 | 1.5 | — | — | — |
| Na Hydroxide | 6.0 | 6.0 | 2.0 | 3.5 | 4.0 | 3.0 |
| Ethanol | 2.0 | 2.0 | 1.0 | 4.0 | 4.0 | 3.0 |
| 1,2 Propanediol | 3.0 | 3.0 | 2.0 | 8.0 | 8.0 | 5.0 |
| Monoethanol-amine | 3.0 | 3.0 | 1.5 | 1.0 | 2.5 | 1.0 |
| TEPAE | 2.0 | 2.0 | — | 1.0 | 1.0 | 1.0 |
| nprE (optional) | 0.03 | 0.05 | — | 0.03 | — | 0.02 |
| PMN | — | — | 0.01 | — | 0.08 | — |
| Protease A (optional) | — | — | 0.01 | — | — | — |
| Lipase | — | — | — | 0.002 | — | — |
| Amylase | — | — | — | — | 0.002 | — |
| Cellulase | — | — | — | — | — | 0.0001 |
| Pectin Lyase | 0.005 | 0.005 | — | — | — | — |
| Aldose Oxidase | 0.05 | — | — | 0.05 | — | 0.02 |
| Galactose oxidase | — | 0.04 | — | — | — | — |
| PAAC | 0.03 | 0.03 | 0.02 | — | — | — |
| DETBCHD | — | — | — | 0.02 | 0.01 | — |
| SRP 1 | 0.2 | 0.2 | — | 0.1 | — | — |
| DTPA | — | — | — | 0.3 | — | — |
| PVNO | — | — | — | 0.3 | — | 0.2 |
| Brightener 1 | 0.2 | 0.2 | 0.07 | 0.1 | — | — |
| Silicone antifoam | 0.04 | 0.04 | 0.02 | 0.1 | 0.1 | 0.1 |
| Balance to 100% perfume/dye and/or water | | | | | | |

Example 11

High Density Dishwashing Detergents Comprising GeoT1

This example provides various formulations for high density dishwashing detergents. In each of these compact formulations, GeoT1 or BCE-GeoT1 is included at a concentration of from about 0.0001 to about 10 weight-percent. In some alternative embodiments, other concentrations will find use, as determined by the formulator, based on their needs.

TABLE 11-1

High Density Dishwashing Detergents

| Compound | Formulations | | | | | |
|---|---|---|---|---|---|---|
| | I | II | III | IV | V | VI |
| STPP | — | 45.0 | 45.0 | — | — | 40.0 |
| 3Na Citrate 2H$_2$O | 17.0 | — | — | 50.0 | 40.2 | — |
| Na Carbonate | 17.5 | 14.0 | 20.0 | — | 8.0 | 33.6 |
| Bicarbonate | — | — | — | 26.0 | — | — |
| Silicate | 15.0 | 15.0 | 8.0 | — | 25.0 | 3.6 |
| Metasilicate | 2.5 | 4.5 | 4.5 | — | — | — |
| PB1 | — | — | 4.5 | — | — | — |
| PB4 | — | — | — | 5.0 | — | — |
| Percarbonate | — | — | — | — | — | 4.8 |
| BB1 | — | 0.1 | 0.1 | — | 0.5 | — |
| BB2 | 0.2 | 0.05 | — | 0.1 | — | 0.6 |
| Nonionic | 2.0 | 1.5 | 1.5 | 3.0 | 1.9 | 5.9 |
| HEDP | 1.0 | — | — | — | — | — |
| DETPMP | 0.6 | — | — | — | — | — |
| PAAC | 0.03 | 0.05 | 0.02 | — | — | — |
| Paraffin | 0.5 | 0.4 | 0.4 | 0.6 | — | — |
| nprE (optional) | 0.072 | 0.053 | — | 0.026 | — | 0.01 |
| PMN | — | — | 0.053 | — | 0.059 | — |
| Protease B (opt.) | — | — | — | — | — | 0.01 |
| Amylase | 0.012 | — | 0.012 | — | 0.021 | 0.006 |
| Lipase | — | 0.001 | — | 0.005 | — | — |
| Pectin Lyase | 0.001 | 0.001 | 0.001 | — | — | — |
| Aldose Oxidase | 0.05 | 0.05 | 0.03 | 0.01 | 0.02 | 0.01 |
| BTA | 0.3 | 0.2 | 0.2 | 0.3 | 0.3 | 0.3 |
| Poly-carboxylate | 6.0 | — | — | — | 4.0 | 0.9 |
| Perfume | 0.2 | 0.1 | 0.1 | 0.2 | 0.2 | 0.2 |
| Balance to 100% Moisture and/or Minors* | | | | | | |

*Brightener/dye/SRP1/Na carboxymethylcellulose/photobleach/MgSO$_4$/PVPVI/suds suppressor/high molecular PEG/clay.
The pH of Examples 11(I) through (VI) is from about 9.6 to about 11.3.

Example 12

Tablet Dishwashing Detergent Compositions Comprising GeoT1

This example provides various tablet dishwashing detergent formulations. The following tablet detergent compositions of the present disclosure are prepared by compression of a granular dishwashing detergent composition at a pressure of 13 KN/cm$^2$ using a standard 12 head rotary press. In each of these formulations, GeoT1 or BCE-GeoT1 is included at a concentration of from about 0.0001 to about 10 weight-percent. In some alternative embodiments, other concentrations will find use, as determined by the formulator, based on their needs.

TABLE 12-1

Tablet Dishwashing Detergent Compositions

| Compound | I | II | III | IV | V | VI | VII | VIII |
|---|---|---|---|---|---|---|---|---|
| STPP | — | 48.8 | 44.7 | 38.2 | — | 42.4 | 46.1 | 46.0 |
| 3Na Citrate 2H$_2$O | 20.0 | — | — | — | 35.9 | — | — | — |
| Na Carbonate | 20.0 | 5.0 | 14.0 | 15.4 | 8.0 | 23.0 | 20.0 | — |
| Silicate | 15.0 | 14.8 | 15.0 | 12.6 | 23.4 | 2.9 | 4.3 | 4.2 |
| Lipase | 0.001 | — | 0.01 | — | 0.02 | — | — | — |
| Protease B (optional) | 0.01 | — | — | — | — | — | — | — |
| Protease C (optional) | — | — | — | — | — | 0.01 | — | — |
| nprE (optional) | 0.01 | 0.08 | — | 0.04 | — | 0.023 | — | 0.05 |
| PMN | — | — | 0.05 | — | 0.052 | — | 0.023 | — |
| Amylase | 0.012 | 0.012 | 0.012 | — | 0.015 | — | 0.017 | 0.002 |
| Pectin Lyase | 0.005 | — | — | 0.002 | — | — | — | — |
| Aldose Oxidase | — | 0.03 | — | 0.02 | 0.02 | — | 0.03 | — |
| PB1 | — | — | 3.8 | — | 7.8 | — | — | 4.5 |
| Percarbonate | 6.0 | — | — | 6.0 | — | 5.0 | — | — |
| BB1 | 0.2 | — | 0.5 | — | 0.3 | 0.2 | — | — |
| BB2 | — | 0.2 | — | 0.5 | — | — | 0.1 | 0.2 |
| Nonionic | 1.5 | 2.0 | 2.0 | 2.2 | 1.0 | 4.2 | 4.0 | 6.5 |
| PAAC | 0.01 | 0.01 | 0.02 | — | — | — | — | — |
| DETBCHD | — | — | — | 0.02 | 0.02 | — | — | — |
| TAED | — | — | — | — | — | 2.1 | — | 1.6 |
| HEDP | 1.0 | — | — | 0.9 | — | 0.4 | 0.2 | — |
| DETPMP | 0.7 | — | — | — | — | — | — | — |
| Paraffin | 0.4 | 0.5 | 0.5 | 0.5 | — | — | 0.5 | — |
| BTA | 0.2 | 0.3 | 0.3 | 0.3 | 0.3 | 0.3 | 0.3 | — |
| Polycarboxylate | 4.0 | — | — | — | 4.9 | 0.6 | 0.8 | — |
| PEG 400-30,000 | — | — | — | — | — | 2.0 | — | 2.0 |
| Glycerol | — | — | — | — | — | 0.4 | — | 0.5 |
| Perfume | — | — | — | 0.05 | 0.2 | 0.2 | 0.2 | 0.2 |
| Balance to 100% Moisture and/or Minors* | | | | | | | | |

*Brightener/SRP1/Na carboxymethylcellulose/photobleach/MgSO$_4$/PVPVI/suds suppressor/high molecular PEG/clay.
The pH of Examples 12(I) through 12(VII) is from about 10 to about 11.5; pH of 12(VIII) is from 8-10. The tablet weight of Examples 12(I) through 12(VIII) is from about 20 grams to about 30 grams.

Example 13

Liquid Hard Surface Cleaning Detergents Comprising GeoT1

This example provides various formulations for liquid hard surface cleaning detergents. In each of these formulations, GeoT1 or BCE-GeoT1 is included at a concentration of from about 0.0001 to about 10 weight-percent. In some alternative embodiments, other concentrations will find use, as determined by the formulator, based on their needs.

TABLE 13-1

Liquid Hard Surface Cleaning Detergents

| Compound | I | II | III | IV | V | VI | VII |
|---|---|---|---|---|---|---|---|
| C$_9$-C$_{11}$E$_5$ | 2.4 | 1.9 | 2.5 | 2.5 | 2.5 | 2.4 | 2.5 |
| C$_{12}$-C$_{14}$E$_5$ | 3.6 | 2.9 | 2.5 | 2.5 | 2.5 | 3.6 | 2.5 |
| C$_7$-C$_9$E$_6$ | — | — | — | — | 8.0 | — | — |
| C$_{12}$-C$_{14}$E$_{21}$ | 1.0 | 0.8 | 4.0 | 2.0 | 2.0 | 1.0 | 2.0 |
| LAS | — | — | — | 0.8 | 0.8 | — | 0.8 |
| Sodium culmene sulfonate | 1.5 | 2.6 | — | 1.5 | 1.5 | 1.5 | 1.5 |
| Isachem ® AS | 0.6 | 0.6 | — | — | — | 0.6 | — |
| Na$_2$CO$_3$ | 0.6 | 0.13 | 0.6 | 0.1 | 0.2 | 0.6 | 0.2 |
| 3Na Citrate 2H$_2$O | 0.5 | 0.56 | 0.5 | 0.6 | 0.75 | 0.5 | 0.75 |
| NaOH | 0.3 | 0.33 | 0.3 | 0.3 | 0.5 | 0.3 | 0.5 |
| Fatty Acid | 0.6 | 0.13 | 0.6 | 0.1 | 0.4 | 0.6 | 0.4 |
| 2-butyl octanol | 0.3 | 0.3 | — | 0.3 | 0.3 | 0.3 | 0.3 |
| PEG DME-2000 ® | 0.4 | — | 0.3 | 0.35 | 0.5 | — | — |
| PVP | 0.3 | 0.4 | 0.6 | 0.3 | 0.5 | — | — |
| MME PEG (2000) ® | — | — | — | — | — | 0.5 | 0.5 |
| Jeffamine ® ED-2001 | — | 0.4 | — | 0.5 | — | — | — |
| PAAC | — | — | — | 0.03 | 0.03 | 0.03 | — |
| DETBCHD | 0.03 | 0.05 | 0.05 | — | — | — | — |
| nprE (optional) | 0.07 | — | 0.08 | 0.03 | — | 0.01 | 0.04 |
| PMN | — | 0.05 | — | — | 0.06 | — | — |
| Protease B (optional) | — | — | — | — | — | 0.01 | — |
| Amylase | 0.12 | 0.01 | 0.01 | — | 0.02 | — | 0.01 |
| Lipase | — | 0.001 | — | 0.005 | — | 0.005 | — |
| Pectin Lyase | 0.001 | — | 0.001 | — | — | — | 0.002 |
| ZnCl$_2$ | 0.02 | 0.01 | 0.03 | 0.05 | 0.1 | 0.05 | 0.02 |
| Calcium Formate | 0.03 | 0.03 | 0.01 | — | — | — | — |
| PB1 | — | 4.6 | — | 3.8 | — | — | — |
| Aldose Oxidase | 0.05 | — | 0.03 | — | 0.02 | 0.02 | 0.05 |
| Balance to 100% perfume/dye and/or water | | | | | | | |

The pH of Examples 13(I) through (VII) is from about 7.4 to about 9.5.

What is claimed is:

1. A detergent composition, comprising:
    a lipase from *Geobacillus stearothermophilus* strain T1 (GeoT1), wherein the lipase is a fusion protein comprising a *Bacillus* strain CBS 670.93 (BCE103) cellulase amino-terminal fragment, and
    a surfactant,
    wherein the detergent composition is more effective in removing oily stains from a surface to be cleaned than the detergent composition with the surfactant in the absence of the lipase.

2. The detergent composition of claim 1, wherein the lipase comprises an amino acid sequence having at least 90% amino acid sequence identity to SEQ ID NO: 4 or to SEQ ID NO: 5.

3. The detergent composition of claim 2, wherein the lipase comprises an amino acid sequence having at least 95% amino acid sequence identity to SEQ ID NO: 4 or to SEQ ID NO: 5.

4. The detergent composition of claim 1, wherein the lipase is a recombinant lipase.

5. The detergent composition claim 1, wherein the lipase is a recombinant lipase expressed in *Bacillus subtilis*.

6. The detergent composition of claim 1, wherein the lipase is a recombinant lipase expressed in *Streptomyces lividans*.

7. The detergent composition of claim 1, wherein the surfactant is one or more surfactants selected from the group consisting of an anionic surfactant, a cationic surfactant, a zwitterionic surfactant, and a combination thereof.

8. The detergent composition of claim 1, wherein the surfactant comprises one or more surfactants selected from the group consisting of sodium dodecyl benzene sulfonate, sodium hydrogenated cocoate, sodium laureth sulfate, C12-14 pareth-7, C12-15 pareth-7, sodium C12-15 pareth sulfate, and C14-15 pareth-4.

9. The detergent composition of claim 1, formulated at a pH of from about 8.0 to about 10.0.

10. The detergent composition of claim 1, wherein the detergent composition is selected from the group consisting of a laundry detergent, a dishwashing detergent, and a hard-surface cleaning detergent.

11. The detergent composition of claim 1, wherein the composition is in a form selected from the group consisting of a liquid, a powder, a granulated solid, and a tablet.

12. The detergent composition of claim 1, wherein the detergent composition is effective in hydrolyzing a lipid at a temperature of from about 30° C. to about 40° C.

13. The detergent composition of claim 1, wherein the detergent composition is more effective in hydrolyzing C4 to C16 substrates compared to an equivalent detergent composition comprising *Pseudomonas pseudoalcaligenes* lipase variant M21L (LIPOMAX™) in place of *G. stearothermophilus* lipase.

14. The detergent composition of claim 1, further comprising a protease.

15. The detergent composition of claim 14, further comprising a subtilisin protease.

16. A method for hydrolyzing a lipid present in a soil or stain on a surface, comprising contacting the surface with a detergent composition of claim 1.

17. A method for performing a transesterification reaction, comprising contacting a donor molecule with a detergent composition of claim 1.

* * * * *

SEQUENCE LISTING

<160> NUMBER OF SEQ ID NOS: 5

<210> SEQ ID NO 1
<211> LENGTH: 1213
<212> TYPE: DNA
<213> ORGANISM: Geobacillus stearothermophilus

<400> SEQUENCE: 1

| | | | | | | |
|---|---|---|---|---|---|---|
| actgcgctag | ccggccccccc | ggcacaggcc | gccagcctcc | gcgccaacga | cgcccccatc | 60 |
| gtgctgctcc | acgtttcac | gggctggggg | cgggaggaga | tgttcggctt | caagtactgg | 120 |
| ggcggcgtgc | gcggggacat | cgagcagtgg | ctgaacgaca | acggctaccg | cacgttcacg | 180 |
| ctggccgtcg | gccccctctc | ctccaactgg | gaccgcgcct | gcgaggcgta | cgcgcagctg | 240 |
| gtcggcggca | cggtcgacta | cggggcggcc | cacgcggcca | agcacggcca | cgcccggttc | 300 |
| ggtcggacgt | acccgggcct | gctgccgag | ctgaagcgcg | gtggccgcat | ccacatcatc | 360 |
| gcgcacagcc | agggcggcca | gacggcccgc | atgctggtca | gcctgctcga | gaacgggtcc | 420 |
| caggaggagc | gcgagtacgc | caaggcccac | aacgtcagcc | tgtcgccgct | gttcgaaggc | 480 |
| gggcaccact | tcgtgctgtc | cgtgacgacc | atcgccaccc | cgcacgacgg | taccaccctc | 540 |
| gtgaacatgg | tcgacttcac | cgaccgcttc | ttcgacctcc | agaaggcggt | gctgaggcg | 600 |
| gcggccgtcg | cctccaacgt | gccgtacacc | tcgcaggtct | acgacttcaa | gctggaccag | 660 |
| tggggcctcc | ggcgccagcc | gggggagagc | ttcgaccact | acttcgagcg | cctgaagcgg | 720 |
| tccccggtgt | ggacctccac | ggacaccgcg | cgctacgacc | tcagcgtgtc | cggcgccgag | 780 |
| aagctgaacc | agtgggtcca | ggcgtcgccc | aacacctact | acctctcgtt | cagcaccgag | 840 |
| cggacctacc | gcgcgcgct | gaccgggaac | cactacccccg | agctgggtat | gaacgccttc | 900 |
| agcgcggtcg | tgtgcgcgcc | gttcctgggg | tcgtaccgga | acccgacgct | gggcatcgac | 960 |
| gaccgctggc | tggagaacga | cggcatcgtc | aacacggtca | gcatgaacgg | tccgaagcgg | 1020 |
| ggctcgagcg | accggatcgt | cccctacgac | ggcaccctga | agaagggcgt | ctggaacgac | 1080 |
| atgggcacct | acaacgtcga | ccacctggag | atcatcggcg | tggaccccgaa | cccgtccttc | 1140 |
| gacatccgcg | cgttctacct | gcggctggcg | gaacagctgg | cgtccctgca | gccctgacaa | 1200 |
| tggggatccg | cga | | | | | 1213 |

<210> SEQ ID NO 2
<211> LENGTH: 1189
<212> TYPE: DNA
<213> ORGANISM: Geobacillus stearothermophilus

<400> SEQUENCE: 2

| | | | | | | |
|---|---|---|---|---|---|---|
| ggatccagac | gatgaggcat | ctcttcgcgc | taacgatgca | cctatcgttc | ttttacacgg | 60 |
| cttcaccggt | tggggacgcg | aagaaatgtt | cggtttcaaa | tactggggag | gcgttagagg | 120 |
| cgatatcgaa | caatggttaa | cgataacgg | ataccgcaca | ttcactcttg | cagtaggccc | 180 |
| gttatctagc | aactgggatc | gtgcttgtga | agcatatgca | caacttgttg | gcggaacagt | 240 |
| agattacggt | gctgcacacg | cggctaaaca | cggacatgct | agattcggtc | gcacataccc | 300 |
| gggattactt | cctgaactga | aaagaggcgg | acgcatccac | atcattgcac | actctcaagg | 360 |
| tggacaaaca | gctagaatgt | tagttagcct | tttagaaaac | ggctctcaag | aagaacgtga | 420 |
| atacgcaaaa | gctcacaacg | taagcctttc | acctttattc | gagggaggtc | accacttcgt | 480 |
| tttgagcgta | acaactatcg | caacacctca | cgatggcaca | actcttgtaa | acatggttga | 540 |

-continued

```
tttcacagat agattcttcg atttacaaaa agctgtactt gaagctgcgg cagttgctag      600
caacgtacct tacacatctc aagtttacga tttcaaatta gatcaatggg gccttcgcag      660
acaaccagga gaatcatttg atcactactt cgagcgttta aaagaagcc ctgtttggac       720 ttctactgat acagcacgct acgacttaag cgttagcggc gctgaaaaac ttaaccaatg      780
ggtacaagca tctcctaaca catactacct tagcttctca acagaaagaa cttaccgcgg      840
agctttaaca ggcaaccact acccagaact tggcatgaac gcgttcagcg ctgttgtatg      900
cgcacctttc ctaggttctt accgcaaccc aacattaggt atcgatgata gatggcttga     960
aaacgatggt atcgttaaca cagtaagcat gaacggaccc aaacgcggga gctctgatag     1020
aatcgttcct tatgatggta cacttaagaa aggagtatgg aacgatatgg gtacatacaa     1080
cgttgatcat ttagaaatta tcggagtaga tccaaacccct tcttttgata ttagagcttt    1140
ctaccttcgt ttagcagaac aacttgcttc tctgcagcct taaaagctt                 1189
```

<210> SEQ ID NO 3
<211> LENGTH: 2118
<212> TYPE: DNA
<213> ORGANISM: Artificial
<220> FEATURE:
<223> OTHER INFORMATION: synthetic polynucleotide encoding a fusion
      protein

<400> SEQUENCE: 3

```
gatgattatt cagttgtaga ggaacatggg caactaagta ttagtaacgg tgaattagtc       60
aatgaacgag gcgaacaagt tcagttaaaa gggatgagtt cccatggttt gcaatggtac      120
ggtcaatttg taaactatga aagcatgaaa tggctaagag atgattgggg ataaactgta     180
ttccgagcag caatgtatac ctcttcagga ggatatattg acgatccatc agtaaaggaa      240
aaagtaaaag agactgttga ggctgcgata gaccttggca tatatgtgat cattgattgg     300
catatccttt cagacaatga cccgaatata tataaagaag aagcgaagga tttctttgat     360
gaaatgtcag agttgtatgg agactatccg aatgtgatat acgaaattgc aaatgaaccg      420
aatggtagtg atgttacgtg ggacaatcaa ataaaaccgt atgcagaaga agtgattccg     480
gttattcgtg acaatgaccc taataacatt gttattgtag gtacaggtac atggagtcag     540
gatgtccatc atgcagccga taatcagctt gcagatccta acgtcatgta tgcatttcat      600
ttttatgcag gaacacatgg acaaaattta cgagaccaag tagattatgc attagatcaa     660
ggagcagcga tatttgttag tgaatggggg acaagtgcag ctacaggtga tggtggtgtg      720 ttttagatg aagcacaagt gtggattgac tttatggatg aaagaaattt aagctgggcc      780
aactggtctc taacgcataa ggatgagtca tctgcagcgt taatgccagg tgcaaatcca      840
actggtggtt ggacagaggc tgaactatct ccatctggta catttgtgag ggaaaaaata     900
agagaatcag catctgacaa caatgatccc ataccggatc cagacgatga ggcatctctt     960
cgcgctaacg atgcacctat cgttctttta cacggcttca ccggttgggg acgcgaagaa     1020
atgttcggtt tcaaatactg gggaggcgtt agaggcgata tcgaacaatg gttaaacgat     1080 aacgatacc gcacattcac tcttgcagta ggcccgttat ctagcaactg ggatcgtgct     1140
tgtgaagcat atgcacaact tgttggcgga acagtagatt acggtgctgc acacgcggct      1200
aaacacggac atgctagatt cggtcgcaca tacccggat tacttcctga actgaaaga      1260 ggcggacgca tccacatcat tgcacactct caaggtggac aaacagctag aatgttagtt      1320 agcctttttag aaaacggctc tcaagaagaa cgtgaatacg caaagctca caacgtaagc     1380 cttttcacctt tattcgaggg aggtcaccac ttcgttttga gcgtaacaac tatcgcaaca    1440
```

```
cctcacgatg gcacaactct tgtaaacatg gttgatttca cagatagatt cttcgattta   1500
caaaaagctg tacttgaagc tgcggcagtt gctagcaacg taccttacac atctcaagtt   1560
tacgatttca aattagatca atggggcctt cgcagacaac caggagaatc atttgatcac   1620
tacttcgagc gttaaaaag aagccctgtt tggacttcta ctgatacagc acgctacgac    1680
ttaagcgtta gcggcgctga aaacttaac caatgggtac aagcatctcc taacacatac    1740
taccttagct tctcaacaga aagaacttac cgcggagctt aacaggcaa ccactaccca    1800 gaacttggca tgaacgcgtt cagcgctgtt gtatgcgcac ctttcctagg ttcttaccgc   1860
aacccaacat taggtatcga tgatagatgg cttgaaaacg atggtatcgt aacacagta    1920 agcatgaacg gacctaaacg cgggagctct gatagaatcg ttccttatga tggtacactt   1980
aagaaaggag tatggaacga tatgggtaca tacaacgttg atcatttaga aattatcgga   2040
gtagatccaa acccttcttt tgatattaga gctttctacc ttcgtttagc agaacaactt   2100
gcttctctgc agccttaa                                                 2118
```

<210> SEQ ID NO 4
<211> LENGTH: 388
<212> TYPE: PRT
<213> ORGANISM: Geobacillus stearothermophilus

<400> SEQUENCE: 4

```
Ala Ser Leu Arg Ala Asn Asp Ala Pro Ile Val Leu His Gly Phe
1               5                   10                  15

Thr Gly Trp Gly Arg Glu Glu Met Phe Gly Phe Lys Tyr Trp Gly Gly
                20                  25                  30

Val Arg Gly Asp Ile Glu Gln Trp Leu Asn Asp Asn Gly Tyr Arg Thr
            35                  40                  45

Phe Thr Leu Ala Val Gly Pro Leu Ser Ser Asn Trp Asp Arg Ala Cys
        50                  55                  60

Glu Ala Tyr Ala Gln Leu Val Gly Gly Thr Val Asp Tyr Gly Ala Ala
65                  70                  75                  80

His Ala Ala Lys His Gly His Ala Arg Phe Gly Arg Thr Tyr Pro Gly
                85                  90                  95

Leu Leu Pro Glu Leu Lys Arg Gly Gly Arg Ile His Ile Ile Ala His
                100                 105                 110

Ser Gln Gly Gly Gln Thr Ala Arg Met Leu Val Ser Leu Leu Glu Asn
            115                 120                 125

Gly Ser Gln Glu Glu Arg Glu Tyr Ala Lys Ala His Asn Val Ser Leu
        130                 135                 140

Ser Pro Leu Phe Glu Gly Gly His His Phe Val Leu Ser Val Thr Thr
145                 150                 155                 160

Ile Ala Thr Pro His Asp Gly Thr Thr Leu Val Asn Met Val Asp Phe
                165                 170                 175

Thr Asp Arg Phe Phe Asp Leu Gln Lys Ala Val Leu Glu Ala Ala Ala
            180                 185                 190

Val Ala Ser Asn Val Pro Tyr Thr Ser Gln Val Tyr Asp Phe Lys Leu
        195                 200                 205

Asp Gln Trp Gly Leu Arg Arg Gln Pro Gly Glu Ser Phe Asp His Tyr
    210                 215                 220

Phe Glu Arg Leu Lys Arg Ser Pro Val Trp Thr Ser Thr Asp Thr Ala
225                 230                 235                 240

Arg Tyr Asp Leu Ser Val Ser Gly Ala Glu Lys Leu Asn Gln Trp Val
                245                 250                 255
```

```
Gln Ala Ser Pro Asn Thr Tyr Tyr Leu Ser Phe Ser Thr Glu Arg Thr
            260                 265                 270

Tyr Arg Gly Ala Leu Thr Gly Asn His Tyr Pro Glu Leu Gly Met Asn
        275                 280                 285

Ala Phe Ser Ala Val Val Cys Ala Pro Phe Leu Gly Ser Tyr Arg Asn
    290                 295                 300

Pro Thr Leu Gly Ile Asp Asp Arg Trp Leu Glu Asn Asp Gly Ile Val
305                 310                 315                 320

Asn Thr Val Ser Met Asn Gly Pro Lys Arg Gly Ser Ser Asp Arg Ile
                325                 330                 335

Val Pro Tyr Asp Gly Thr Leu Lys Lys Gly Val Trp Asn Asp Met Gly
            340                 345                 350

Thr Tyr Asn Val Asp His Leu Glu Ile Ile Gly Val Asp Pro Asn Pro
        355                 360                 365

Ser Phe Asp Ile Arg Ala Phe Tyr Leu Arg Leu Ala Glu Gln Leu Ala
    370                 375                 380

Ser Leu Gln Pro
385

<210> SEQ ID NO 5
<211> LENGTH: 705
<212> TYPE: PRT
<213> ORGANISM: Artificial
<220> FEATURE:
<223> OTHER INFORMATION: synthetic fusion protein

<400> SEQUENCE: 5

Asp Asp Tyr Ser Val Val Glu Glu His Gly Gln Leu Ser Ile Ser Asn
1               5                   10                  15

Gly Glu Leu Val Asn Glu Arg Gly Glu Gln Val Gln Leu Lys Gly Met
            20                  25                  30

Ser Ser His Gly Leu Gln Trp Tyr Gly Gln Phe Val Asn Tyr Glu Ser
        35                  40                  45

Met Lys Trp Leu Arg Asp Asp Trp Gly Ile Thr Val Phe Arg Ala Ala
    50                  55                  60

Met Tyr Thr Ser Ser Gly Gly Tyr Ile Asp Asp Pro Ser Val Lys Glu
65              70                  75                  80

Lys Val Lys Glu Thr Val Glu Ala Ala Ile Asp Leu Gly Ile Tyr Val
                85                  90                  95

Ile Ile Asp Trp His Ile Leu Ser Asp Asn Asp Pro Asn Ile Tyr Lys
            100                 105                 110

Glu Glu Ala Lys Asp Phe Phe Asp Glu Met Ser Glu Leu Tyr Gly Asp
        115                 120                 125

Tyr Pro Asn Val Ile Tyr Glu Ile Ala Asn Glu Pro Asn Gly Ser Asp
    130                 135                 140

Val Thr Trp Asp Asn Gln Ile Lys Pro Tyr Ala Glu Glu Val Ile Pro
145                 150                 155                 160

Val Ile Arg Asp Asn Asp Pro Asn Asn Ile Val Ile Val Gly Thr Gly
                165                 170                 175

Thr Trp Ser Gln Asp Val His His Ala Ala Asp Asn Gln Leu Ala Asp
            180                 185                 190

Pro Asn Val Met Tyr Ala Phe His Phe Tyr Ala Gly Thr His Gly Gln
        195                 200                 205

Asn Leu Arg Asp Gln Val Asp Tyr Ala Leu Asp Gln Gly Ala Ala Ile
    210                 215                 220
```

```
Phe Val Ser Glu Trp Gly Thr Ser Ala Ala Thr Gly Asp Gly Val
225                 230                 235                 240

Phe Leu Asp Glu Ala Gln Val Trp Ile Asp Phe Met Asp Glu Arg Asn
            245                 250                 255

Leu Ser Trp Ala Asn Trp Ser Leu Thr His Lys Asp Glu Ser Ser Ala
                260                 265                 270

Ala Leu Met Pro Gly Ala Asn Pro Thr Gly Gly Trp Thr Glu Ala Glu
            275                 280                 285

Leu Ser Pro Ser Gly Thr Phe Val Arg Glu Lys Ile Arg Glu Ser Ala
            290                 295                 300

Ser Asp Asn Asn Asp Pro Ile Pro Asp Pro Asp Glu Ala Ser Leu
305                 310                 315                 320

Arg Ala Asn Asp Ala Pro Ile Val Leu Leu His Gly Phe Thr Gly Trp
                325                 330                 335

Gly Arg Glu Glu Met Phe Gly Phe Lys Tyr Trp Gly Gly Val Arg Gly
            340                 345                 350

Asp Ile Glu Gln Trp Leu Asn Asp Asn Gly Tyr Arg Thr Phe Thr Leu
            355                 360                 365

Ala Val Gly Pro Leu Ser Ser Asn Trp Asp Arg Ala Cys Glu Ala Tyr
            370                 375                 380

Ala Gln Leu Val Gly Gly Thr Val Asp Tyr Gly Ala Ala His Ala Ala
385                 390                 395                 400

Lys His Gly His Ala Arg Phe Gly Arg Thr Tyr Pro Gly Leu Leu Pro
                405                 410                 415

Glu Leu Lys Arg Gly Gly Arg Ile His Ile Ile Ala His Ser Gln Gly
            420                 425                 430

Gly Gln Thr Ala Arg Met Leu Val Ser Leu Leu Glu Asn Gly Ser Gln
            435                 440                 445

Glu Glu Arg Glu Tyr Ala Lys Ala His Asn Val Ser Leu Ser Pro Leu
450                 455                 460

Phe Glu Gly Gly His His Phe Val Leu Ser Val Thr Thr Ile Ala Thr
465                 470                 475                 480

Pro His Asp Gly Thr Thr Leu Val Asn Met Val Asp Phe Thr Asp Arg
                485                 490                 495

Phe Phe Asp Leu Gln Lys Ala Val Leu Glu Ala Ala Val Ala Ser
            500                 505                 510

Asn Val Pro Tyr Thr Ser Gln Val Tyr Asp Phe Lys Leu Asp Gln Trp
            515                 520                 525

Gly Leu Arg Arg Gln Pro Gly Glu Ser Phe Asp His Tyr Phe Glu Arg
            530                 535                 540

Leu Lys Arg Ser Pro Val Trp Thr Ser Thr Thr Ala Arg Tyr Asp
545                 550                 555                 560

Leu Ser Val Ser Gly Ala Glu Lys Leu Asn Gln Trp Val Gln Ala Ser
                565                 570                 575

Pro Asn Thr Tyr Tyr Leu Ser Phe Ser Thr Glu Arg Thr Tyr Arg Gly
            580                 585                 590

Ala Leu Thr Gly Asn His Tyr Pro Glu Leu Gly Met Asn Ala Phe Ser
            595                 600                 605

Ala Val Val Cys Ala Pro Phe Leu Gly Ser Tyr Arg Asn Pro Thr Leu
            610                 615                 620

Gly Ile Asp Asp Arg Trp Leu Glu Asn Asp Gly Ile Val Asn Thr Val
625                 630                 635                 640

Ser Met Asn Gly Pro Lys Arg Gly Ser Ser Asp Arg Ile Val Pro Tyr
                645                 650                 655
```

```
Asp Gly Thr Leu Lys Lys Gly Val Trp Asn Asp Met Gly Thr Tyr Asn
            660             665                 670

Val Asp His Leu Glu Ile Ile Gly Val Asp Pro Asn Pro Ser Phe Asp
        675             680             685

Ile Arg Ala Phe Tyr Leu Arg Leu Ala Glu Gln Leu Ala Ser Leu Gln
    690             695                 700

Pro
705
```